US008489336B2

(12) United States Patent
Arakelyan et al.

(10) Patent No.: US 8,489,336 B2
(45) Date of Patent: Jul. 16, 2013

(54) TECHNIQUES FOR PURPOSING A NEW COMPOUND AND FOR RE-PURPOSING A DRUG

(75) Inventors: Levon Arakelyan, Ashdod (IL); Vera Selitser, Jerusalem (IL); Zvia Agur, Tel Aviv (IL); Tali Eilam Tzoreff, Herzliya (IL)

(73) Assignee: Optimata Ltd., Ramat Gan (IL)

( * ) Notice: Subject to any disclaimer, the term of this patent is extended or adjusted under 35 U.S.C. 154(b) by 342 days.

(21) Appl. No.: 12/621,175

(22) Filed: Nov. 18, 2009

(65) Prior Publication Data

US 2010/0161301 A1    Jun. 24, 2010

Related U.S. Application Data

(63) Continuation-in-part of application No. 10/662,345, filed on Sep. 16, 2003, now Pat. No. 7,970,550, and a continuation-in-part of application No. PCT/IB2008/003162, filed on May 19, 2008.

(60) Provisional application No. 60/410,803, filed on Sep. 16, 2002, provisional application No. 60/924,533, filed on May 18, 2007.

(51) Int. Cl.
*G06F 19/00*       (2011.01)
(52) U.S. Cl.
USPC ........................................................ 702/19
(58) Field of Classification Search
None
See application file for complete search history.

(56) References Cited

U.S. PATENT DOCUMENTS

| 5,657,255 | A | 8/1997 | Fink et al. |
| 5,808,918 | A | 9/1998 | Fink et al. |
| 6,041,788 | A | 3/2000 | Shen |
| 6,081,786 | A | 6/2000 | Barry et al. |

FOREIGN PATENT DOCUMENTS

| WO | 97/44752 A1 | 11/1997 |
| WO | 01/00083 A1 | 1/2001 |
| WO | 02/051354 A2 | 7/2002 |

OTHER PUBLICATIONS

Holford et al. (Ann. Rev. Pharmacol. Toxicol. (2000) vol. 40, pp. 209-234).*
Rooney et al. (DDT (2001). vol. 6, No. 5, pp. 802-806).*
O'Connor et al. (Nature Reviews (2005) vol. 4, pp. 1005-1014).*
FDA, Center for Drug Evaluation and Research (CDER), Drug Development Process for Investigational New Drugs, http://www.fda.gov/cder/handbook/develop.htm., pp. 3-28, Mar. 6, 1998.
Department of Health and Human Services, FDA, International Conference on Harmonisation; Guidance on General Considerations for Clinical Trials, Federal Register Wednesday, Dec. 17, 1997, 62(242):66113-66119.
E.A. Eisenhauer et al., "Phase I Clinical Trial Design in Cancer Drug Development", Journal of Clinical Oncology, 2000, 18(3):684-692.
Richard Simon et al., "Accelerated Titration Designs for Phase I Clinical Trials in Oncology", Journal of the National Cancer Institute, 1997, 89(15):1138-1147.
Jerry M. Collins et al., "Potential Roles for Preclinical Pharmacology in Phase I Clinical Trials", Cancer Treatment Reports, 1986, 70(1):73-80.
Zvia Agur et al., "Effect of the Dosing Interval on Myelotoxicity and Survival in Mice Treated by Cytarabine", Eur. J. Cancer, 1992, 28A(6/7):1085-1090.
Lutzy Cojocaru et al., "A Theoretical Analysis of Interval Drug Dosing for Cell-Cycle-Phase-Specific Drugs", Mathematical Biosciences, 1992, 109:85-97.
Paolo Ubezio et al., "Increasing 1-β-D-Arabinofuranosylcytosine Efficacy by Scheduled Dosing Intervals Based on Direct Measurements of Bone Marrow Cell Kinetics", Cancer Research, 1994, 54:6446-6451.
Z. Agur, "Resonance and Anti-Resonance in the Design of Chemotherapeutic Protocols", Journal of Theoretical Medicine, 1998, 1:237-245.
Z. Agur, "Clinical trials of Zidovudine in HIV infection", Lancet, 1989, 2(8676):1400.
Z. Agur, "Use of mathematical models for analyzing host-specific parasitaemia profiles in African trypanosomes", Parasitology Today, 1992, 8(4):128-129.
R. Norel et al., "A Model for the Adjustment of the Mitotic Clock by Cyclin and MPF Levels", Science, 1991, 251:1076-1078.
Zvia Agur et al., "Zidovudine Toxicity to Murine Bone Marrow May be Affected by the Exact Frequency of Drug Administration", Exp. Hematol., 1991, 19:364-368.
Zvia Agur, "Fixed Points of Majority Rule Cellular Automata with Application to Plasticity and Precision of the Immune System", Complex Systems, 1991, 2:351-357.
Zvia Agur et al., "Maturation of the humoral immune response as an optimization problem", Proc. R. Soc. Land. B., 1991, 245:147-150.
Linda E. Harnevo et al., "Drug resistance as a dynamic process in a model for multistep gene amplification under various levels of selection stringency", Cancer Chemother. Pharmacol., 1992, 30:469-476.
Ramit Mehr et al., "Bone marrow regeneration under cytotoxic drug regimens: behaviour ranging from homeostasis to unpredictability in a model for hemopoietic differentiation", BioSystems, 1992, 26:231-237.
Z. Agur et al., "Pulse mass measles vaccination across age cohorts", Proc. Natl. Acad. Sci. USA, 1993, 90:11698-11702.

(Continued)

*Primary Examiner* — Lori A Clow
(74) *Attorney, Agent, or Firm* — Sughrue Mion, PLLC

(57) ABSTRACT

A method for repurposing a pharmaceutical compound. The method includes identifying a pharmaceutical compound, the pharmaceutical compound corresponding to a drug that has failed in clinical development or an approved drug. A mathematical model describing the physiological processes related to at least one disease and the effects of the pharmaceutical compound on the disease is created. The model is adjusted based upon information from preclinical or clinical trials. A new treatment protocol is suggested to salvage the failed drug or a new way to use an approved drug. The suggested treatment protocol is displayed. Systems and computer program products encompassing the above techniques are also disclosed.

33 Claims, 39 Drawing Sheets

OTHER PUBLICATIONS

Zvia Agur et al., "Use of Knowledge on (øn) Series for Predicting Optimal Chemotherapy Treatment", Random & Computational Dynamics, 1994, 2(3&4):279-286.

Z. Agur et al., "AZT Effect on the Bone Marrow—a New Perspective on the Concorde Trial", Journal of Biological Systems, 1995, 3(1):241-251.

Ramit Mehr et al., "Temporal Stochasticity Leads to Nondeterministic Chaos in a Model for Blood Cell Production", Fluctuations and Order: The New Synthesis, 1996, Springer, New York, pp. 419-427.

Z. Agur, "Mathematical Modelling of Cancer Chemotherapy: Investigation of the Resonance Phenomenon", Adv. in Math. Pop. Dynamics-Molecules, Cells, Man, Series in Math. Biol. 6:571-578, 1998.

D. Hart et al., "The growth law of primary breast cancer as inferred from mammography screening trials data", British Journal of Cancer, 1998, 78(3):382-387.

Eliezer Shochat et al., "Using Computer Simulations for Evaluating the Efficacy of Breast Cancer Chemotherapy Protocols", Mathematical Models and Methods in Applied Sciences, 1999, 9(4):599-615.

Kirill Skomorovski et al., "New TPO treatment schedules of increased safety and efficacy: pre-clinical validation of a thrombopoiesis simulation model", British Journal of Haematology, 2003, 123:683-691.

L. Arakelyan et al., "A computer algorithm describing the process of vessel formation and maturation, and its use for predicting the effects of anti-angiogenic and anti-maturation therapy on vascular tumor growth", Angiogenesis, 2002, 5:203-214.

Richard Simon, "Bayesian Design and Analysis of Active Control Clinical Trials", Biometrics, 1999, 55:484-487.

Richard Simon, "Some Practical Aspects of the Interim Monitoring of Clinical Trials", Statistics in Medicine, 1994, 13:1401-1409.

Richard Simon, "Therapeutic Equivalence Trials", Handbook of Statistics in Clinical Oncology, 2001, Marcel Dekker, New York, pp. 173-187.

Athanassios Iliadis et al., "Optimizing Drug Regimens in Cancer Chemotherapy by an Efficacy-Toxicity Mathematical Model", Computers and Biomedical Research, 2000, 33:211-226.

F.L. Pereira et al., "A new optimization based approach to experimental combination chemotherapy", Frontiers Med. Biol. Engng., 1995, 6(4):257-268.

Christine Veyrat-Follet et al., "Clinical trial simulation of docetaxel in patients with cancer as a tool for dosage optimization", Clin. Pharmacol. Ther., 2000, 68:677-687.

R.S. Acharya et al., "Development of Optimal Drug Administration Strategies for Cancer-Chemotherapy in the Framework of Systems Theory", Int. J. Biomed. Computing, 1984, 15:139-150.

Nigel Stallard et al., "Sequential designs for phase III clinical trials incorporating treatment selection", Statistics in Medicine, 2003, 22:689-703.

J.V.S. Gobburu et al., "Application of modeling and simulation to integrate clinical pharmacology knowledge across a new drug application", International Journal of Clinical Pharmacology and Therapeutics, 2002, 40(7):281-288.

Peter Bauer et al., "Combining Different Phases in the Development of Medical Treatments within a Single Trial", Statistics in Medicine, 1999, 18:1833-1848.

E. Ardizzone et al., "Artificial intelligence techniques for cancer treatment planning", Med. Inform (Lond), 1988, 13(3):199-210.

Donald A. Berry, "Adaptive Trials and Bayesian Statistics in Drug Development", Biopharmaceutical Report, 2001, 9(2):1-11.

Donald A. Berry, "General Keynote: Clinical Trial Design", Gynecologic Oncology, 2003, 88:S114-S116.

Edward Trimble et al., "Discussion: Current Issues in the Design of Ovarian Cancer Treatment Trials", Gynecological Oncology, 2003, 88:S122-S123.

* cited by examiner

Table 1: Profiles of Selected DR Companies

| Company | Sourcing Strategy | Therapeutic Focus |
|---|---|---|
| Arachanova | SwitchBase technology to discover new indications | Predominantly central nervous system (CNS) |
| Arakis | Literature searching | Inflammation |
| Aspreva | Literature searching | Rare diseases |
| BTG | Multi-dimensional sourcing approaches | Multiple |
| CombinatoRx | Combination drug screening | Oncology, inflammation |
| Cypress Biosciences | Literature searching | CNS |
| Dynogen | Management expertise | Gastrointestinal (GI) |
| GeneLogic | Genomics | Technology focus |
| Hypnion | In vitro screening | Sleep disorders |
| KineMed | Screening abandoned clinical compounds | Metabolic diseases |
| Nektar | Drug delivery | Metabolic diseases |
| Somaxon | Management expertise | CNS |
| Sosei | Compound libraries from Japanese companies | GI |
| Vectura | Reformation of existing drugs | CNS |

FIG. 1

Table 2: Biopharmaceutical companies repositioning drugs for neuro

| Company (location) | Therapeutic focus | Approach |
|---|---|---|
| Cypress Bioscience, Inc. (San Diego, California) | Functional somatic syndromes and pain | Leverages expertise in the pathophysiology underlying functional somatic syndromes and their diagnoses and also animal models of fibromyalgia syndrome. |
| Dynogen Pharmaceuticals, Inc. (Boston, Massachusetts and Durham, North Carolina) | Genitourinary and gastrointestinal disorders | Leverages its knowledge of the nexus between neurology and genitourinary and gastrointestinal disorders, as well as its predictive pharmacology models to make informed decisions on potential research and development candidates. |
| Sention, Inc. (Providence, Rhode Island) | Memory impairment and other CNS disorders | Applies a whole-animal assay system that identifies genes and proteins involved in memory consolidation and then identifies known drugs which modulate these targets. |
| Vela Pharmaceuticals, Inc. (Lawrenceville, New Jersey) | IBS, fibromyalgia, anxiety, menopausal symptoms | 'Rediscovers' drugs by reformulating de-prioritized compounds, seeking expanded geographic approval for drugs with limited distribution and exploring possible uses across multiple therapeutic areas. |

FIG. 2

Table 3: Biopharmaceutical companies repositioning drugs for non-neuro

| Company (location) | Therapeutic focus | Approach |
|---|---|---|
| BioMedicines, Inc. (Emoryville, California) | Oncology and hepatitis | 'Redirected development' of compounds bought or licensed from pharmaceutical companies. Biomed 777/Atamestane, acquired from Schering AG in 1999, is in Phase III for breast cancer. |
| Bionaut (Cambridge, Massachusetts) | Cancer and inflammation | Leverages its Sentinel Pathway Reporter System which consists of a library of human cell lines that report the activity of specific disease-associated pathways. |
| ChemGenex Therapeutics Inc. (Menlo Park, California) | Oncology | Uses gene-expression analysis, cellular screening systems and computational medicinal informatics software to recognize chemical structures with unique attributes. |
| CombinatoRx, Inc. (Boston, Massachusetts) | Oncology, inflammation, respiratory, metabolic and infectious diseases | Leverages a high-throughput combination screening system in conjunction with cell-based phenotypic assays to identify combinations of existing compounds able to attach multiple disease pathways. |
| Sosei Co., Ltd. (Tokyo, Japan) | Multiple | Uses an extensive network of biotech collaborations to discover new applications for a library of pre-commercialization stage compounds licensed from various Japanese pharma companies. |

FIG. 3

Patient population response is predicted for each clinical indication considered for phase II The charts below show the predicted response to the original drug schedule

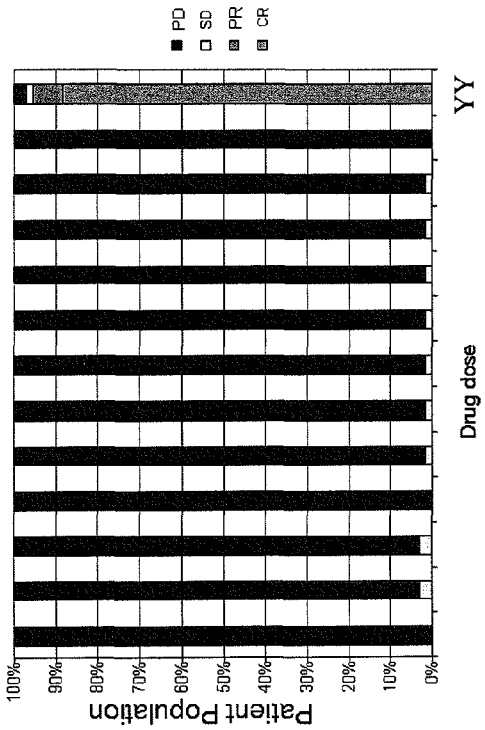

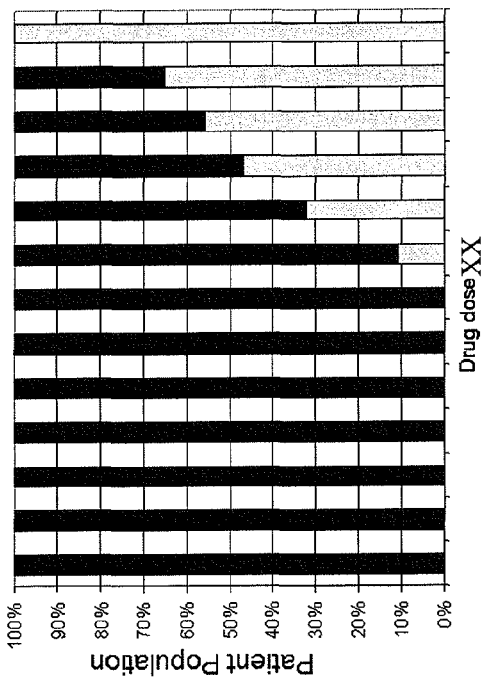

97% partial response in indication B is predicted for a schedule of yy mg administered every 21 days 11% stable disease in indication A is predicted for a schedule of xx mg administered every 21 days

FIG. 5

Simulated Therapies

Single Agent

- D   Doxorubicin (Andriamycne®)
- Doc  Docetaxel (Taxotere®)
- I   CPT-11 (Comptosar®)
- G   Gemcitabine (Gemzar®)
- B   Bevacizumab (Avastin®)
- S   Sunitinib (Sutent®)
- Sor  Sorafenib (Nexavar®)

Combination therapy

- Bevacizumab + Docetaxel
- Bevacizumab + Gemcitabine
- Gemcitabine + Docetaxel
- Bevacizumab + Gemcitabine + Docetaxel
- Bevacizumab + Doxorubicin
- Bevacizumab + CPT-11
- Bevacizumab + Sorafenib

FIG. 11

Optimata has accurately predicted response to various treatment schedules for the MCS patient

| | Regimen | | | | Observed Results | Predicted Results | Accuracy |
|---|---|---|---|---|---|---|---|
| | Drug | Dose (mg/kg) | Route | Schedule | | | |
| 1 | Control | | | | 2.2 | 2 | 91 % |
| 2 | CPT-11 | 100 | IP | Q7Dx3 | 60 % | 64 % | 92 % |
| | Bevacizumab | 10 | IP | Q3Dx10 | | | |
| 3 | Gemcitabine | 40 | IP | Q3Dx4 | 109 % | 63 % | 58 % |
| | Docetaxel | 6.3 | IV | Q2Dx3 | | | |
| | Bevacizumab | 10 | IP | Q3Dx10 | | | |
| 4 | Doxorubicin | 2 | IV | QDx5 | 56 % | 62 % | 91 % |
| | Bevacizumab | 10 | IP | Q3Dx10 | | | |
| 5 | Sorafenib | 60 | PO | QDx10 | 39 % | 34 % | 87 % |
| 6 | Sorafenib | 60 | PO | QDx10 | 87 % | 62 % | 72 % |
| | Bevacizumab | 10 | IP | Q3Dx10 | | | |

Results: Tumor Growth Inhibition (xenografts)
except group 1: ratio of final size (day 22) to initial size Average accuracy: 82 %

FIG. 12

Bevacizumab greatly enhances efficacy in MCS xenografts

| Treatment | Efficacy w/o Bevacizumab | Efficacy w/ Bevacizumab | Δ TGI |
|---|---|---|---|
| TXT | 69 | 92 | +33% |
| TXT+GEM | 71 | 91 | +28% |
| SFN | 44 | 79 | +80% |
| DOX | 41 | 83 | +102% |
| CPT-11 | 40 | 77 | +93% |
| GEM | 1 | 67 | +660% |

Efficacy – best simulated TGI (%)

Docetaxel Q1W+ Bevacizumab Q2W is Most Effecacious of all Tested Schedules (120 day treatment)

A: Bevacizumab 10mg/kg IV inf 90min q14dx9 + Docetaxle 80 mg/m2 IV inf 90min q21dx6
B: Bevacizumab 10mg/kg IV inf 90min q14dx9 + Docetaxle 100 mg/m2 IV inf 90min q21dx6
C: Bevacizumab 10mg/kg IV inf 90min q14dx9 + Docetaxle 43 mg/m2 IV inf 90min (q8dx6+14d rest)x2
D: Bevacizumab 15mg/kg IV inf 90min q14dx9 + Docetaxle 80 mg/m2 IV inf 90min q21dx6
E: Bevacizumab 15mg/kg IV inf 90min q14dx9 + Docetaxle 100 mg/m2 IV inf 90min q21dx6
F: Bevacizumab 15mg/kg IV inf 90min q14dx9 + Docetaxle 43 mg/m2 IV inf 90min (q8dx6+14d rest)x2

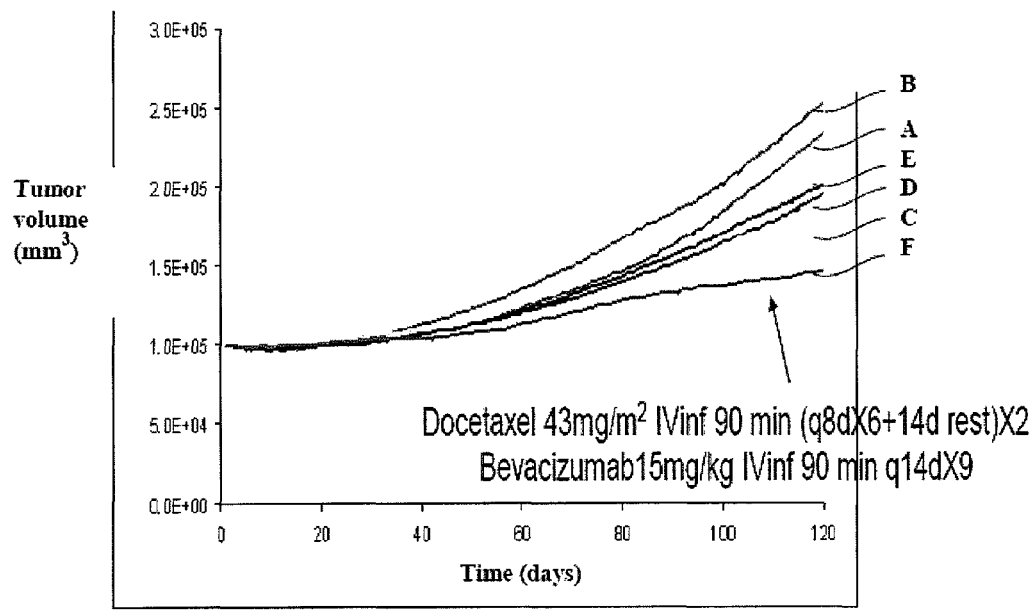

FIG. 14

Sorafenib Combined With Bevacizumab+Docetaxel
Greatly Improves Efficacy (120 day treatment)

A: Bevacizumab 15mg/kg IV inf 90min q14dx9 + Docetaxle 43 mg/m2 IV inf 90min (q8dx6+14d rest)x2
B: Bevacizumab+ Docetaxle as above + Sorafenib 400 mg/m2 PO b.i.d x 120
C: Bevacizumab+ Docetaxle as above + Sorafenib 500 mg/m2 PO b.i.d x 120

TECHNIQUES FOR PURPOSING A NEW COMPOUND AND FOR RE-PURPOSING A DRUG

This is a continuation-in-part of U.S. application Ser. No. 10/662,345 filed Sep. 16, 2003; which claims benefit of U.S. Provisional Patent Application Ser. No. 60/410,803 filed Sep. 16, 2002, and PCT/IB2008/003162 filed May 19, 2008 which is published and which claims benefit of U.S. Provisional Patent Application Ser. No. 60/924,533 filed May 18, 2007; the disclosure of each of which is incorporated herein by reference in their entirety.

The subject matter of this Application is also related to commonly-owned U.S. application Ser. No. 09/691,053 filed Oct. 19, 2000 (which issued as U.S. Pat. No. 6,871,171 on Mar. 22, 2005), U.S. application Ser. No. 10/207,772 filed Jul. 31, 2002 (which issued as U.S. Pat. No. 7,418,374 on Aug. 26, 2008), U.S. application Ser. No. 09/827,229 filed Apr. 6, 2001 (which issued as U.S. Pat. No. 7,133,814 on Nov. 7, 2006), and U.S. application Ser. No. 10/192,001 filed Jul. 10, 2002 (which issued as U.S. Pat. No. 7,266,483 on Sep. 4, 2007), the disclosure of each of which is incorporated herein by reference in their entirety.

I. DESCRIPTION OF THE INVENTION

A. Field of the Invention

The disclosed teachings relate to an interactive technique for purposing and repurposing of a drug. The drug may be any compound in any stage of development and approval, from discovery through an approved marketed drug. It also relates to any compound whose development has been discontinued at any stage of development. The disclosed teachings relates to the prediction and recommendation of the optimal use of a newly developed compound (purposing), or for an improved use of any compound/drug previously purposed (repurposing). Purposing of a drug involves aiming it for specific clinical indications and/or patient populations along with a treatment schedule. In case the drug in question was previously purposed, the repurposing involves another use, that is, a change to the current application of an approved drug or to the intended/tested application of a drug under development. The change in application may involve aiming the drug for a different disease indication or for a new specified patient population. It may also involve the change of the treatment schedule applied/recommended for the drug, including new combination therapy. The disclosed teachings are embodied in systems, methods and computer program products for predicting the progression of biological systems related to diseases in a population, and for prediction and optimization of disease treatment in that population. These systems, methods and computer program products can be implemented for the development of new drugs and for the change in the use of existing drugs.

B. Background of the Invention

The following papers provide useful background information, for which they are incorporated herein by reference in their entirety, and are selectively referred to in the remainder of this disclosure by their accompanying reference numbers in brackets (i.e., [Reference 3] for the third numbered paper by Agur Z et al):

1. Editorial. New estimates of drug development costs. Journal of Health Economics 22 (2003) 325-330.
2. Joseph A. DiMasi, Ronald W. Hansen, Henry G. Grabowski. The price of innovation: new estimates of drug development costs. Journal of Health Economics 22 (2003) 151-185.
3. Agur Z., Ziv I., Shohat R., Wick M., Webb C., Hankins D., Arkelyan L., Sidransky D. Using a novel computer technology for tailoring and chemotherapeutic drug schedules to the individual patient. First AACR International Conference on Molecular Diagnostics in Cancer Therapeutic Development, Sep. 12-15, 2006.
4. CHI Drug Repositioning Summit Philadelphia, Pa., USA. Oct. 16-17, 2006
5. Yvonne Y. Li, Jianghong An, Steven J. M. Jones. A Large-Scale Computational Approach to Drug Repositioning. Genome Informatics 17(2): 239{247 (2006) 239.
6. Kerry A. O'Connor, Bryan L. Roth. Finding new tricks for old drugs: an Nature Review. Drug Discovery 4, 1005-1014 (2005).
7. Thomas Reilly, Nicole Yost. Drug Repositioning. Drug Discovery 2006.
8. U.S. application Ser. No. 10/997,323. Method for high-throughput screening of compounds and combinations of compounds for discovery and quantification of actions, particularly unanticipated therapeutic or toxic actions, in biological systems.
9. David W Carley. Drug Repurposing: Identify, Develop and Commercialize New Uses for Existing or Abandoned Drugs. Part II. 31 Jan.-1 Feb. 2005, Philadelphia, Pa., USA
10. Ashburn, T. T., Thor, K. B. Drug repositioning: identifying and developing new uses for existing drugs. Nature Review. Drug Discovery 3, 673-683 (2004).
11. Drug Development Process for Investigational New Drugs. FDA Center for Drug Evaluation and Research (CDER). www.fda.gov/cder/handbook/develop
12. Department Of Health And Human Services, Food and Drug Administration. International Conference on Harmonization; Guidance on General Considerations for Clinical Trials. Federal Register/Vol. 62, No. 242/ Wed1
13. Dodion P, Kenis Y, Staquet M. Phase-I trials of single agents in adult solid tumours: preclinical and clinical aspects. Drugs Exp Clin Res 1986; 12(1-3):23-30.
14. Fridborg H, Nygren P, Larsson R. Relationship between pharmacokinetic parameters in patients and cytotoxicity in vitro of standard and investigational anticancer drugs. Anticancer Drugs 1995 February; 6(1):64-9.
15. Eisenhauer E A, O'Dwyer P J, Christian M, Humphrey J S. Phase-I clinical trial design in cancer drug development. J Clin Oncol 2000 February; 18(3):684-92.
16. Simon R, Freidlin B, Rubinstein L, Arbuck S G, Collins J, Christian M C. Accelerated titration designs for Phase-I clinical trials in oncology. J Natl Cancer Inst 1997 Aug. 6; 89(15):1138-47.
17. Collins J M, Zaharko D S, Dedrick R L, Chabner B A. Potential roles for preclinical pharmacology in Phase-I clinical trials. Cancer Treat Rep 1986 January; 70(1):73-80.
18. Agur Z., Arnon R., Schechter B. Effect of the dosing interval on survival and myelotoxicity in mice treated by Cytosine arabinoside. Eur. J. Cancer., 28A(6/7), 1992 (pp. 1085-1090).
19. Cojocaru L., Agur Z. Theoretical analysis of interval drug dosing for cell-cycle-phase-specific drugs. Math. Biosci., 109, 1992 (pp. 85-97).
20. Ubezio P., Tagliabue G., Schechter B., Agur Z. Increasing 1-b-D-Arabinofuranosylcytosine efficacy by scheduled dosing intervals based on direct measurement of bone marrow cell kinetics, Cancer Res 54, 1994 (pp. 6446-6451).

21. Agur Z. Resonance and anti-resonance in the design of chemotherapeutic schedules. Jour. Theor. Medicine 1, 1998 (pp. 237-245).
22. Agur Z. Clinical trials of Zidovudine in HIV infection. Lancet 2, 1989, (p. 734).
23. Agur Z. Use of mathematical models for analyzing host-specific parasitaemia profiles in African trypanosomes. Parasitology Today 8, 1992 (pp. 128-129).
24. Norel R., Agur Z. A model for the adjustment of the mitotic clock by cyclin and MPF levels. Science, 251, 1991 (pp. 1076-1078).
25. Agur Z., Anion R., Sandak B., Schechter, B. Zidovudine toxicity to murine bone marrow may be affected by the exact frequency of drug administration. Exp. Hematol., 19, 1991 (pp. 364-368).
26. Agur Z. Fixed points of majority rule cellular automata applied to plasticity and precision of the immune response. Complex Systems, 5, 1991 (pp. 351-356).
27. Agur Z., Mazor G., Meilijson I. Maturation of the humoral immune response as an optimization problem. Proc. R. Soc. Lond. B, 245, 1991 (pp. 147-150).
28. Harnevo L. H., Agur Z. Drug resistance as a dynamic process in a model for multi-step gene amplification under various levels of selection stringency. Cancer Chemo. Pharmacol., 30, 1992 (pp. 469-476).
29. Mehr R., Agur Z. Bone marrow regeneration under cytotoxic drug regimens: behaviour ranging from homeostasis to unpredictability in a model for hemopoietic differentiation. BioSystems, 26/4, 1992 (pp. 231-237).
30. Agur Z., Cojocaru L., Mazor G., Anderson R. M., Danon Y. L. Pulse mass Measles vaccination across age cohorts Proc. Nat. Acad. Sci. USA, 90, 1993 (pp. 11698-11702).
31. Agur Z., Dvir Y. Use of knowledge on $\{\phi n\}$ series for predicting optimal chemotherapy treatment. Random & Computational Dynamics 2(3&4), 1994 (pp. 279-286).
32. Agur Z., Tagliabue G., Schechter B., Ubezio P. AZT effect on the Bone Marrow—a new perspective on the Concorde Trials. Jour. Biol. Sys 3(1), 1995 (pp. 241-251).
33. Mehr R., Agur Z. Temporal stochasticity leads to non-deterministic chaos in a model for blood cell production. p. 419-427 in: Fluctuations and Order: The New Synthesis. (M. M. Millonas ed.) New-York, Springer. 1996.
34. Agur, Z. Mathematical modelling of cancer chemotherapy: investigation of the resonance phenomenon. Advances in Math. Pop Dynamics—Molecules Cells, Man, Series in Math. Biol: (Kimmel and Arino eds) 6, 1998 (pp 543-555).
35. Hart D., Shochat, E.& Agur, Z. The growth law of primary breast cancer tumors as inferred from mammography screening trials. British Journal of Cancer, 78 (3) 1998 (pp. 382-387).
36. Shochat, E. Hart, D & Agur, Z. Using Computer Simulations for Evaluating The Efficacy of Breast Cancer Chemotherapy Protocols Jour. Math. Models & Methods in Applied Sciences Vol. 9 (4) 1999 (pp. 599-615).
37. Agur, Z. Hassin, R and Levy, S. Optimizing chemotherapy scheduling using local search heuristics. Operations Research. 2006 September; 54 (5) 2006 (pp. 829-846).
38. Skomorovski K., Harpak H., Ianovski A., Vardi M., Visser TP., Hartong S., Van Vliet H., Wagemaker G., Agur Z. New TPO treatment schedules of increased safety and efficacy: pre clinical validation of a thrombopoiesis simulation model. Br. Jour. Haematol, 123 (4), 2003 (pp. 683-691).
39. Arakelyan L, Vainstain V, and Agur Z. A computer algorithm describing angiogenesis and vessel maturation and its use for studying the effects of anti-angiogenic and anti-maturation therapy on vascular tumor growth. Angiogenesis. 5 2002 (pp. 203-214).
40. Simon R. Bayesian design and analysis of active controlled clinical trials. Biometrics 1999; 55:484-487.
41. Simon R. Some practical aspects of the interim monitoring of clinical trials. Statistics in Medicine 1994; 13:1401-1409.
42. Simon R. Therapeutic equivalence trials. Handbook of Statistics in Clinical Oncology 2001; 173-188.

Drug development is a lengthy and expensive process. It costs up to US $900 million for a big pharmaceutical company to develop a successful drug [Reference 1]. About 75 percent to 80 percent of the cost [Reference 2, p. 165 "out-of-pocket clinical period cost per approved new drug is US $282 million and the capitalized clinical period cost per approved new drug is US $467 million."] and about 60 percent of the time to develop a drug are spent in the clinical phases of development [Reference 2 p. 166]. Many compounds are tested in clinical trials but clinical trial failure rate exceeds 80% [Reference 1 p. 326]. Thus, compounds abandoned in a later phase of clinical trials usually involve loss of tens of millions of dollars.

However, the classical method of clinical trials design [[References 11, 12] suffers major drawbacks. On the one hand, developing drugs by "trial and error" alone can not guarantee that the selected schedules are better than other, yet to be tried, treatment regimens. On the other hand, the number of schedules which can be empirically tested is negligibly small with respect to the potential number of sensible schedules.

Research shows that the effects of the drug may crucially correlate with the internal dynamics of the tumor growth processes, as well as with the relevant patient's physiology. These aspects might often be too complex to be estimated by the naked eye, and slight nuances in the treatment schedule may be critical for the effect achieved [[References 18-21]. In theory, if all potential treatment schedules could be tested, considering all the available information on the involved biological processes, pathological processes and the momentary effect of the drug on every element of these processes, one could, a-priori, suggest a theoretical set of the most promising treatment schedules for a given indication, or, even, for a given patient. Subsequently, these promising schedules would be clinically tested, thus saving human resources and time, and helping to achieve maximal possible therapeutic effects of the tested drug.

Needless to say that such methods would enable to rehabilitate drugs with valid properties, which failed during the development process, due to insufficient efficacy, or limitations of toxicity, which could possibly be overcome by modifying the treatment schedule. In addition, these methods would enable a "GO-NOGO" decision to be made early during the clinical trial process.

Thus, it is critical to choose, as early as possible, the target indications for which the drug may be approved, preferably prior to the onset of clinical trials. Once clinical trials have started and a compound has failed, it is of great importance that the drug be salvaged by a switch either to a new indication, a new patient population or a new treatment schedule. As phase I is conducted to assess the safety, tolerability, pharmacodynamics and pharmacokinetics of the drug, usually it does not have to be repeated in order to test the drug for different indications or patient populations. Consequently, such changes may turn the drug successful without the need for going through the whole process of clinical trials from the very start.

Drug repurposing, i.e., determination of novel uses for existing drugs and rescuing failed compounds, has many benefits. The major benefits of this approach include shorter development cycles, faster drug approval, and the ability to capitalize on the repertoire of drug candidates. As a consequence, many pharmaceutical and biotech companies have adopted and incorporated it in their business model.

Different approaches may be taken in order to allow drug repurposing. The following were recently presented at the CHI Drug repositioning Summit [Reference 4]. Some companies and research institutions relate to the original drug mechanism. Some use the SOSA approach, namely, Selective Optimization of Side Activities of drug molecule. Some use in-vivo and in-vitro [Reference 6] high throughput approaches. Some use in-silico tools which involve mainly data mining and high throughput screening tools.

For example:

Canada's Michael Smith Genome Sciences Centre

Li et al [Reference 5] used prediction of protein-small molecule interactions and applied it to the drug repositioning problem through a large-scale analysis of known drug targets and small molecule drugs.

Gene Logic uses reverse-chemical genetics (i.e., Target->Compound->Disease->Drug), to study transcription profiles of drug targets in normal and disease contexts to determine correlative effects between regulation and plausible links to new therapeutic areas.

Melior Discovery uses in-vivo phenotypic screening approach. Compounds are chosen based on clinical safety and chemical attractiveness, and the experimental phenotypic screening is not biased toward mechanism.

Inpharmatica's approach relies on data-mining of a carefully curated database of drugs, their approved indications, affinities, selectivity, and molecular targets.

CombinatoRx systematically screens combinations of known compounds and identifies non-obvious combinations with novel patterns of activity, as combinations provide the multiple levers needed to modify several targets in a disease network simultaneously.

FIG. 1 includes a table provided by reference 7 listing selected drug repurposing companies and their strategy. FIG. 2 includes a table provided by reference 10 listing some more drug repurposing companies and their approach.

U.S. application Ser. No. 10/997,323 titled: "Method for high-throughput screening of compounds and combinations of compounds for discovery and quantification of actions, particularly unanticipated therapeutic or toxic actions, in biological systems" discloses methods to measure and quantify molecular flux rates through metabolic pathways (synthesis and breakdown or input and removal rates from pools of molecules) in vivo as targets of drug action.

Definitions

For ease of understanding of the present specification, the following abbreviations/notations are used:

$A_1$-$A_3$—constants
$B_1$-$B_3$—constants
BL—blood
c—elevation increment of drug concentration
$C_{Di}$—the concentration after administrating the given dose in blood
$C_{Dij}$—the concentration after administering the given dose "i" in target tissue "j"
$C_{Dik}$—the concentration after administering the given dose "i" in toxicity tissue "k"
$C_I$—drug concentration
CmC—a control group for combinational therapy (patients treated by today's first line therapy)
CT—clinical trial
d—elevation increment of the drug dose
$D_0(PhI)$—initial dose proposed for Phase I clinical trial
$D_i$—dose administered
DLT—dose limiting toxicity
$D_n$—dose for a given variant of the protocol proposed by the model for testing
$D_o$-$D_f$—initial dose to final dose,
EC—effective concentration
$E_{ci}$—effect of the drug at the given concentration
$E_{cij}$—effect of the drug at the given concentration "i" on target tissue "j"
$E_{Cdik}$—effect of the drug at the administered dose "i" on toxicity tissue "k"
$EC_n$—effective concentration n, the concentration giving n percent of maximal effect
ED—effective dose
$E_{Dij}$—the efficacy after administering the given dose "i" in target tissue "j"
F1, F2, F3—counters
$G_O$—a rationale to continue developing the drug
Group Ci—group of patients for combinational treatment by protocol I (CTPi) for indication cancer type I (CTi)
Group Mi—group of patients for monotherapy treatment by protocol I (MTPi) for indication cancer type I (CTi)
h—of human tissue/cell culture
$h_{tc}$—human tumor cells
K1, K2—counters
$LD_n$—lethal dose n, i.e. a dose causing n percent of death in the tested animals group
MA, MB, MC—number of tests in which the drug effect remains<X, when escalating concentrations, for stopping further dose escalation
MED—Minimum Effective Dose, a dose at which the effect was first observed
MnC—a standard monotherapy treatment group (patients treated by today's first line therapy)
MTD—maximal tolerated dose (after which the DLT is observed)
$n_1$—number of steps to be defined in order to going from mED to MTD;
$n_2$—number of steps to be defined to go from mED to RD
nr—nonrodent species
NO GO—no rationale to continue developing the drug.
P—percent of animals that died
PD—pharmacodynamics
PK—pharmacokinetics
r—of rodent tissue/cell culture
$r/h_{Tox}$—rodent or human toxicity
$r_{tc}$—rodent tumor cells
RD—recommended dose
$s_1$-$s_2$—constants
$T_n$—dose interval for a given variant of the protocol proposed by the model for testing
Tox—the tissue in which a toxic effect occurs ("toxicity" tissue)
TT—target tissue
VPE—Virtual Patient Engine X—accepted threshold ("asymptote") of differences in the effect after elevation of concentration by one increment (c).

Z1, Z2, Z3—counters

II. SUMMARY OF THE INVENTION

The above discussed advantages may be realized by a method for repurposing a pharmaceutical compound. The method comprises identifying a pharmaceutical compound, the pharmaceutical compound corresponding to a drug that has failed in clinical development or an approved drug. A computer model describing the physiological processes related to at least one disease and the effects of the pharmaceutical compound on the disease is created. The computer model is adjusted based upon information from preclinical or clinical trials. A new treatment protocol is recommended to salvage the failed drug or a new way to use an approved drug. The recommended treatment protocol is displayed. The computer model is an in silico patient that is adjusted according to the results of the pre-clinical and clinical trials.

In an embodiment of the invention, a method for repurposing a pharmaceutical compound, resulting in a new treatment protocol to salvage a failed drug or an approved drug, comprises identifying a pharmaceutical compound, wherein the pharmaceutical compound is a drug that has failed in clinical development or an approved drug, creating a computer model for pharmacokinetics and pharmacodynamics of the drug from in vitro or in vivo data obtained from administration of at least a single dose of the drug from a pre-clinical trial wherein the computer model created is adjusted based on data from in vitro or in vivo studies in animals, performing computer simulations using the computer model with data obtained from administration of different doses of the drug and dosing intervals for different indications and patient populations in at least one phase I clinical trial, wherein the computer model is an in silico patient that is adjusted according to results of the pre-clinical trial or the at least one phase I clinical trial.

In a specific embodiment, the new treatment protocol is based on at least one component selected from the group consisting of new regimen, new drug combination, new disease, new patient population, and use of biomarkers represented in the computer model to differentiate between responders and non-responders in the patient population.

In another specific embodiment, the new disease is cancer.

In another specific embodiment, the new disease is a hematological disorder.

In another specific embodiment, the new disease is a hematological disorder that is related to cancer.

In another specific embodiment, the new treatment protocol reduces drug toxicity.

In another specific embodiment, the new treatment protocol increases drug efficacy.

In another specific embodiment, new treatment protocol increases drug efficacy and reduces drug toxicity.

In another specific embodiment, the computer simulations of the model are performed prior to the phase I clinical trial, to predict results of the phase I clinical trial, and the predicted results are compared to the phase I clinical trial results and the computer model is adjusted based on the comparison.

In an even more specific embodiment, the at least a single dose is incrementally increased in at least one dose escalation step.

In another even more specific embodiment, the dose escalation step may be calculated by computer simulations performed using the computer model in step (a) to obtain a maximal tolerated dose, minimum effective dose, and a recommended dose.

In another specific embodiment, the computer model is adjusted based on whether the clinical trial indicates a result higher than a threshold in at least one of pre-clinical trial and phase I clinical trial.

Another embodiment of the invention is a method for repurposing a pharmaceutical compound, resulting in a new treatment protocol to salvage a failed drug or an approved drug, the method comprising creating a computer model for pharmacokinetics and pharmacodynamics of a drug that has failed in clinical development or an approved drug from in vitro or in vivo data obtained from administration of at least a single dose of the drug from at least one clinical trial to predict one or more clinical outcomes, wherein the prediction of one or more clinical outcomes is compared with clinical results at least from at least one clinical trial and the comparison is used to adjust the computer model, wherein the computer model is an in silico patient that is adjusted according to the clinical results at least from at least one pre-clinical trial, and wherein a new treatment protocol to salvage the failed drug or the approved drug is determined based on computer simulation results.

In a specific embodiment, the clinical results are further at least from at least one clinical trial selected from the group consisting of pre-clinical trial, phase I clinical trial, phase II clinical trial, phase III clinical trial, and phase IV clinical trial.

Another embodiment of the invention is a method for repurposing a pharmaceutical compound, resulting in a new treatment protocol to salvage a failed drug or an approved drug, the method comprising creating a computer model for pharmacokinetics and pharmacodynamics of a drug that has failed in clinical development or an approved drug from in vitro or in vivo data obtained from administration of at least a single dose of the drug from at least one clinical trial to predict one or more clinical outcomes, wherein the prediction of one or more clinical outcomes is compared with clinical results at least from at least one clinical trial and the comparison is used to adjust the computer model, wherein the computer model is an in silico patient that is adjusted according to the clinical results at least from at least one phase I clinical trial, and wherein a new treatment protocol to salvage the failed drug or the approved drug is determined based on results of the computer simulation predictions.

In a specific embodiment, the clinical results are further at least from at least one clinical trial selected from the group consisting of pre-clinical trial, phase I clinical trial, phase II clinical trial, phase III clinical trial, and phase IV clinical trial.

In another specific embodiment of the invention, at least a single dose is administered in a dose-escalation during phase I clinical trial.

Another embodiment of the invention is a method for repurposing a pharmaceutical compound, resulting in a new treatment protocol to salvage a failed drug or an approved drug, the method comprising creating a computer model for pharmacokinetics and pharmacodynamics of a drug that has failed in clinical development or an approved drug from in vitro or in vivo data obtained from administration of at least a single dose of the drug from at least one clinical trial to predict one or more clinical outcomes; wherein the prediction of one or more clinical outcomes is compared with clinical results at least from at least one clinical trial and the comparison is used to adjust the computer model, wherein the computer model is an in silico patient that is adjusted according to the clinical results at least from at least one phase II clinical trial, and wherein a new treatment protocol to salvage the failed drug or the approved drug is determined based on the computer simulation results.

In a specific embodiment, the clinical results are further at least from at least one clinical trial selected from the group consisting of pre-clinical trial, phase I clinical trial, phase II clinical trial, phase III clinical trial, and phase IV clinical trial.

Another embodiment of the invention is a method for repurposing a pharmaceutical compound, resulting in a new treatment protocol to salvage a failed drug or an approved drug, the method comprising creating a computer model for pharmacokinetics and pharmacodynamics of a drug that has failed in clinical development or an approved drug from in vitro or in vivo data obtained from administration of at least a single dose of the drug from at least one clinical trial to predict one or more clinical outcomes, wherein the prediction of one or more clinical outcomes is compared with clinical results at least from at least one clinical trial and the comparison is used to adjust the computer model, wherein the computer model is an in silico patient that is adjusted according to the clinical results at least from at least one phase III clinical trial, and wherein a new treatment protocol to salvage the failed drug or the approved drug is determined based on the computer simulation results.

In a specific embodiment, the clinical results are further at least from at least one clinical trial selected from the group consisting of pre-clinical trial, phase I clinical trial, phase II clinical trial, phase III clinical trial, and phase IV clinical trial.

Another embodiment of the invention is a method for repurposing a pharmaceutical compound, resulting in a new treatment protocol to salvage a failed drug or an approved drug, the method comprising creating a computer model for pharmacokinetics and pharmacodynamics of a drug that has failed in clinical development or an approved drug from in vitro or in vivo data obtained from administration of at least a single dose of the drug from at least one clinical trial to predict post-marketing efficacy of the drug, and long term efficacy of the drug, resulting in prediction of one or more clinical outcomes, wherein the prediction of one or more clinical outcomes is compared with clinical results at least from at least one clinical trial and the comparison is used to adjust the computer model, wherein the computer model is an in silico patient that is adjusted according to the clinical results at least from at least one phase IV clinical trial, and wherein a new treatment protocol to salvage the failed drug or the approved drug is determined based on the computer simulation results.

In a specific embodiment, the clinical results are further at least from at least one clinical trial selected from the group consisting of pre-clinical trial, phase I clinical trial, phase II clinical trial, phase III clinical trial, and phase IV clinical trial.

Another aspect of the invention is a system for repurposing a pharmaceutical compound, the system comprising: identifying a pharmaceutical compound, wherein the pharmaceutical compound is a drug that has failed in clinical development or an approved drug, a computer model for pharmacokinetics and pharmacodynamics of the drug is created based on data of effects of the drug administered in vitro or in vivo to determine the physiological effect of the drug on a disease, a model adjustor that adjusts the computer model based upon results of computer simulations from at least one pre-clinical or at least one clinical trial, and a treatment protocol generator that determines a new treatment protocol to salvage the drug that has failed in a clinical development or the approved drug.

Another aspect of the invention is a computer program product comprising a computer readable media having instructions that allows a computer to implement a process comprising identifying a pharmaceutical compound, the pharmaceutical compound corresponding to a drug that has failed in clinical development or an approved drug, creating a computer model for pharmacokinetics and pharmacodynamics of the drug is created based on data of effects of the drug administered in vitro or in vivo to determine the physiological effect of the drug on a disease, adjusting the computer model based upon results of computer simulations from at least one pre-clinical or at least one clinical trial, determining a new treatment protocol to salvage the failed drug or the approved drug based on the results of computer simulation results, and displaying the new treatment protocol in an output window.

III. BRIEF DESCRIPTION OF THE DRAWINGS

The above objectives and advantages of the disclosed teachings will become more apparent by describing in detail preferred embodiment thereof with reference to the attached drawings in which:

FIG. 1 shows Table 1: Profiles of Selected DR Companies

FIG. 2 shows Table 2 listing Biopharmaceutical companies repositioning drugs for neuro.

FIG. 3 shows Table 3 listing Biopharmaceutical companies repositioning drugs for non-neuro.

FIG. 5 shows the predicted response to the drug schedule suggested by the pharmaceutical company in both indications

FIG. 11 shows a list of simulated drugs.

FIG. 12 shows a table of experimental and predicted results of treated and untreated tumor xenografts, demonstrating prediction accuracy.

FIG. 14 shows tumor growth following various schedules of Docetaxel and Bevacizumab over 120 day treatment.

FIG. 20B-E show various stages of an example implementation.

Figure 21:
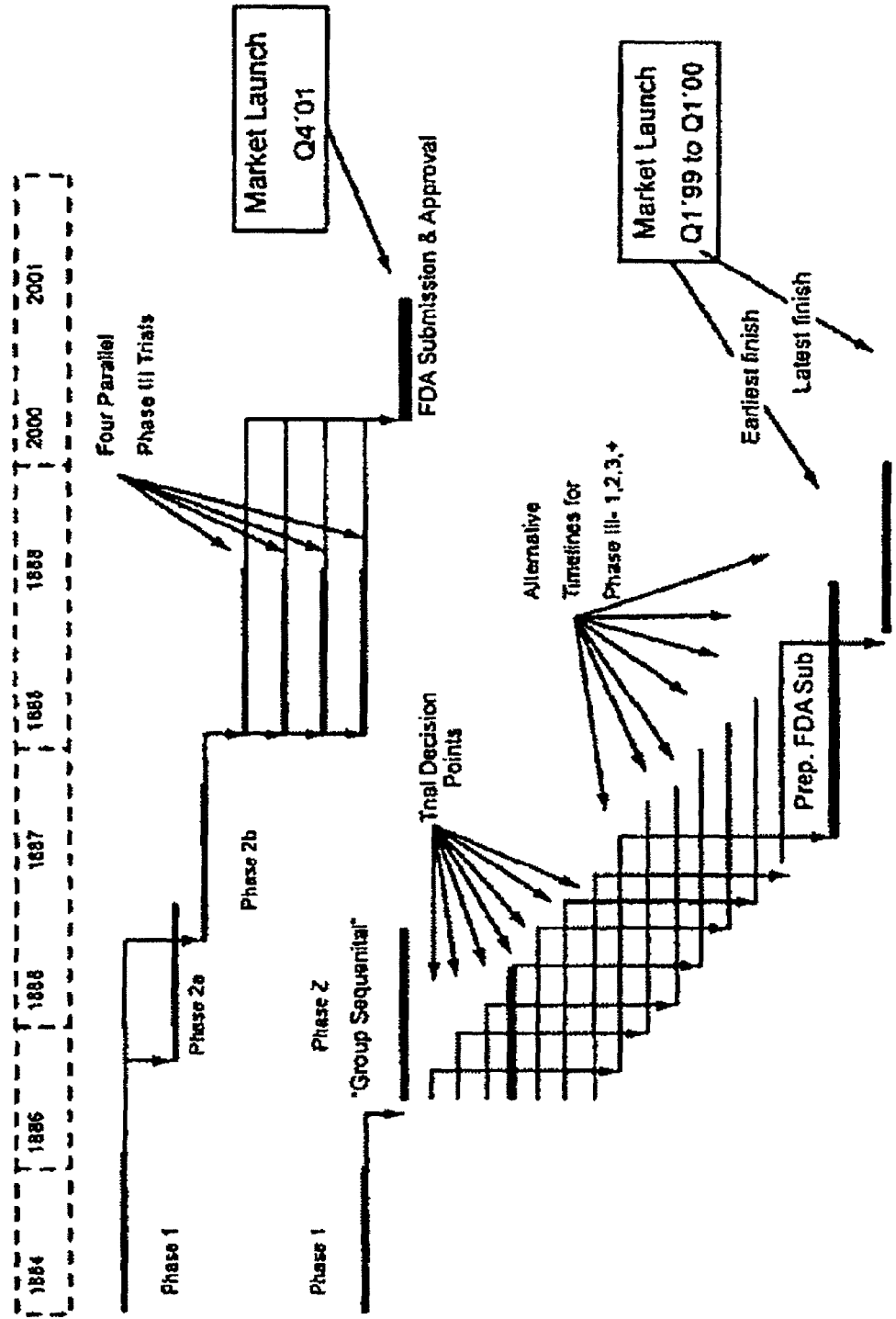

FIG. 21 shows an example of adaptive trial design as compared to the classical design.

Figure 22A:
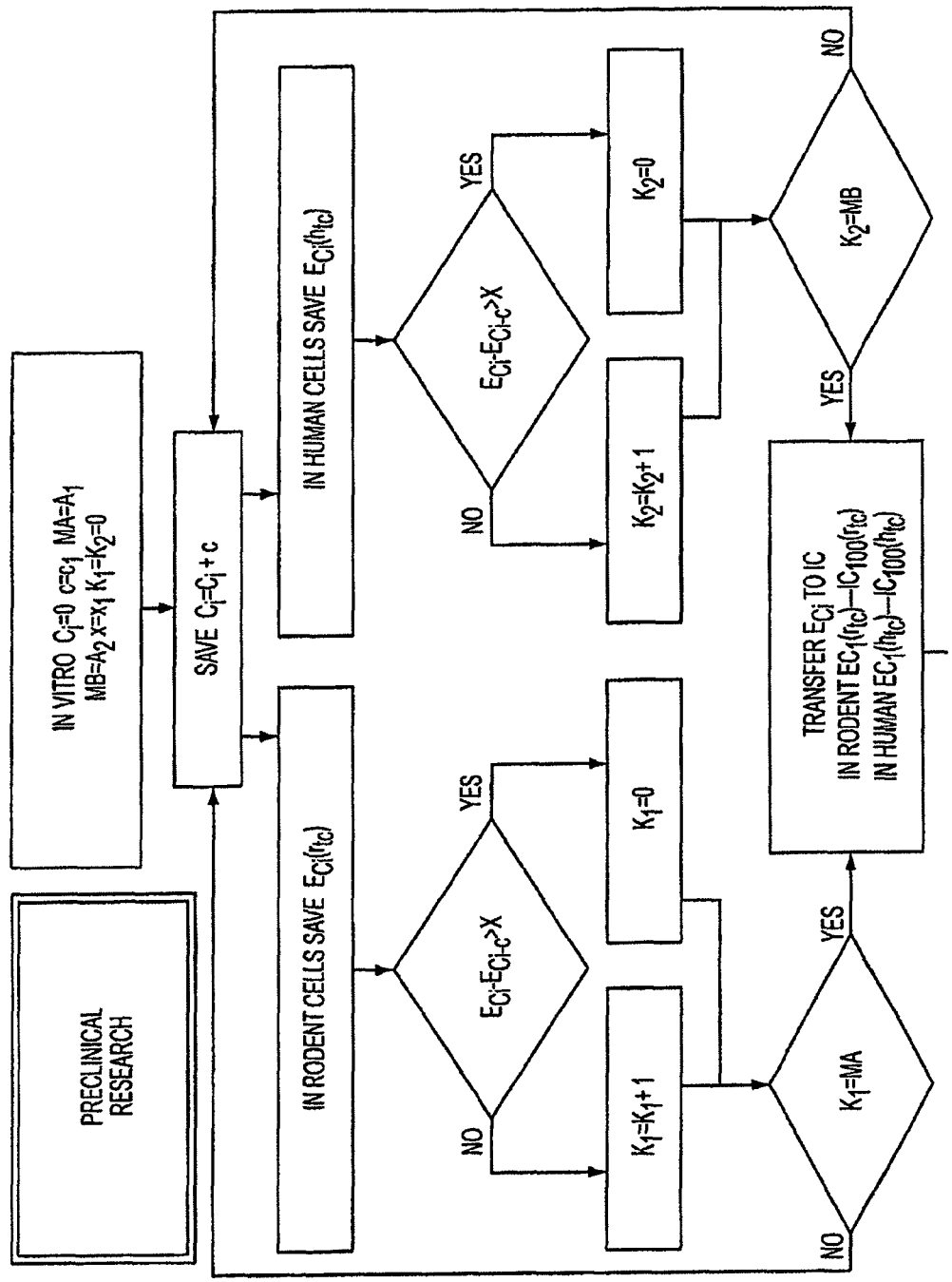

FIG. 22A shows a panel of an example implementation of the disclosed interactive trial design in the preclinical research stage.

Figure 22B:
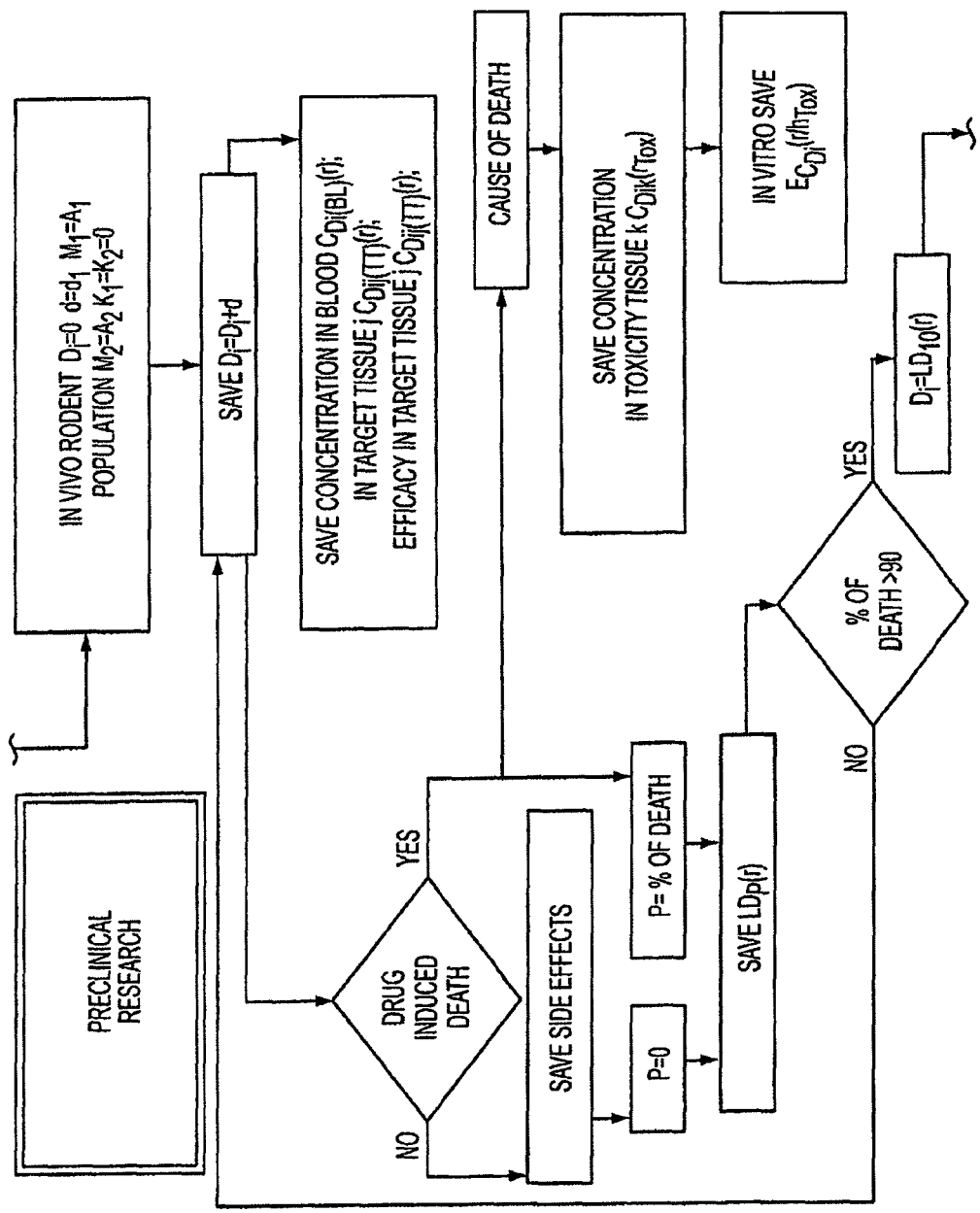

FIG. 22B shows a panel of an example implementation of the disclosed interactive trial design in the preclinical research stage.

Figure 22C:
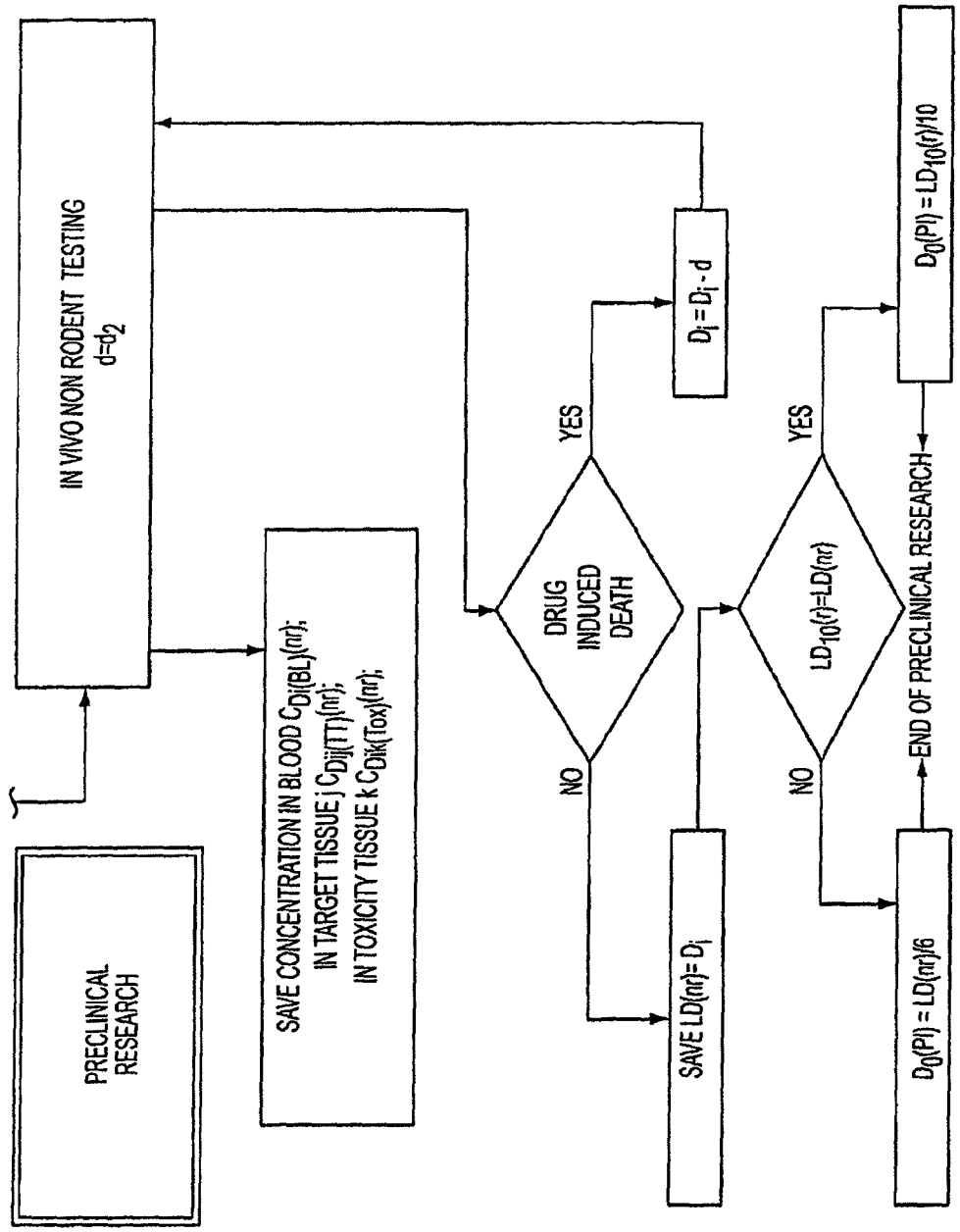

FIG. 22C shows one panel of an example implementation of the disclosed interactive trial design in the preclinical research stage.

Figure 22D:
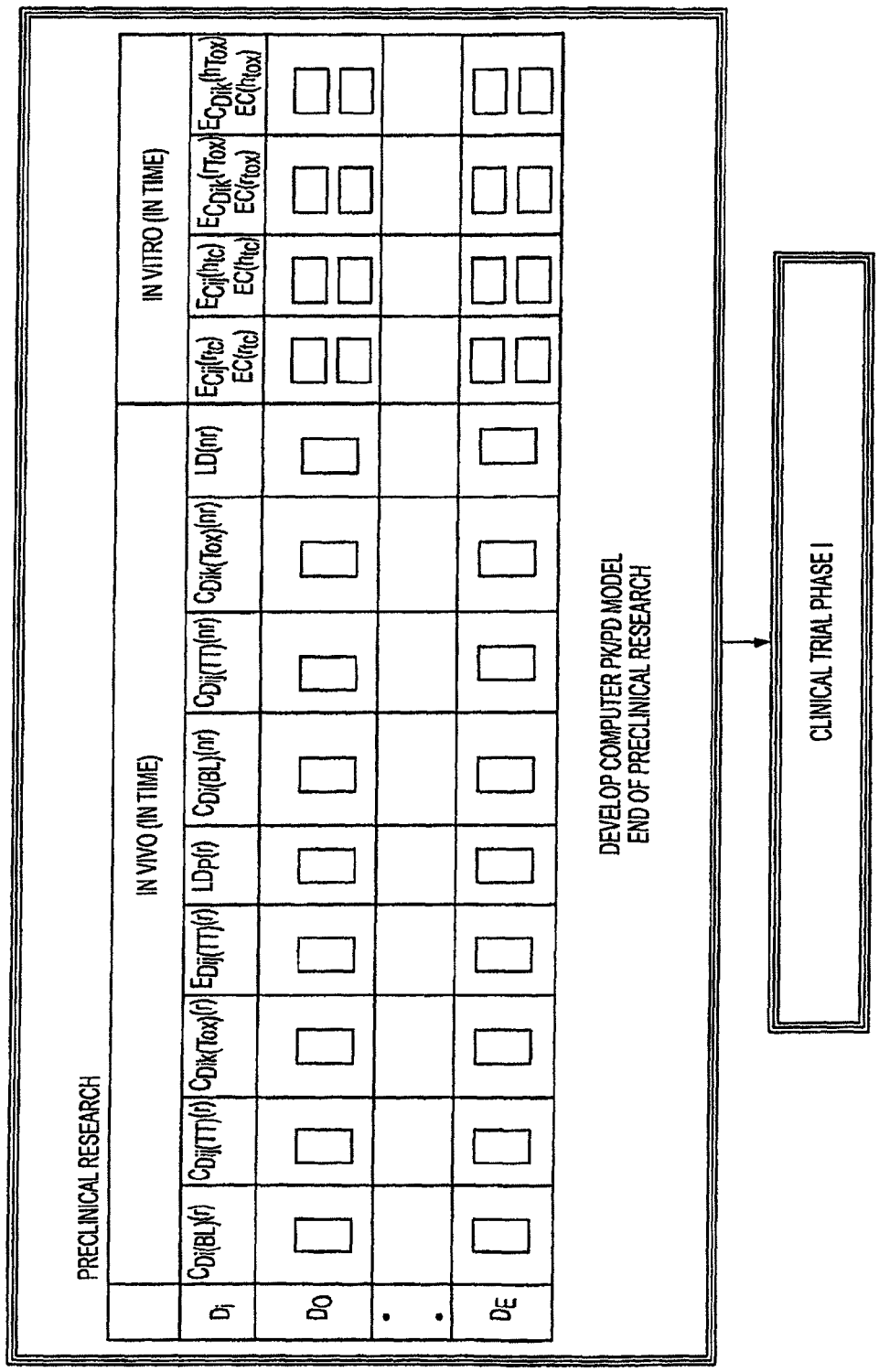

FIG. 22D shows a summary of the preclinical research stage.

Figure 22E:
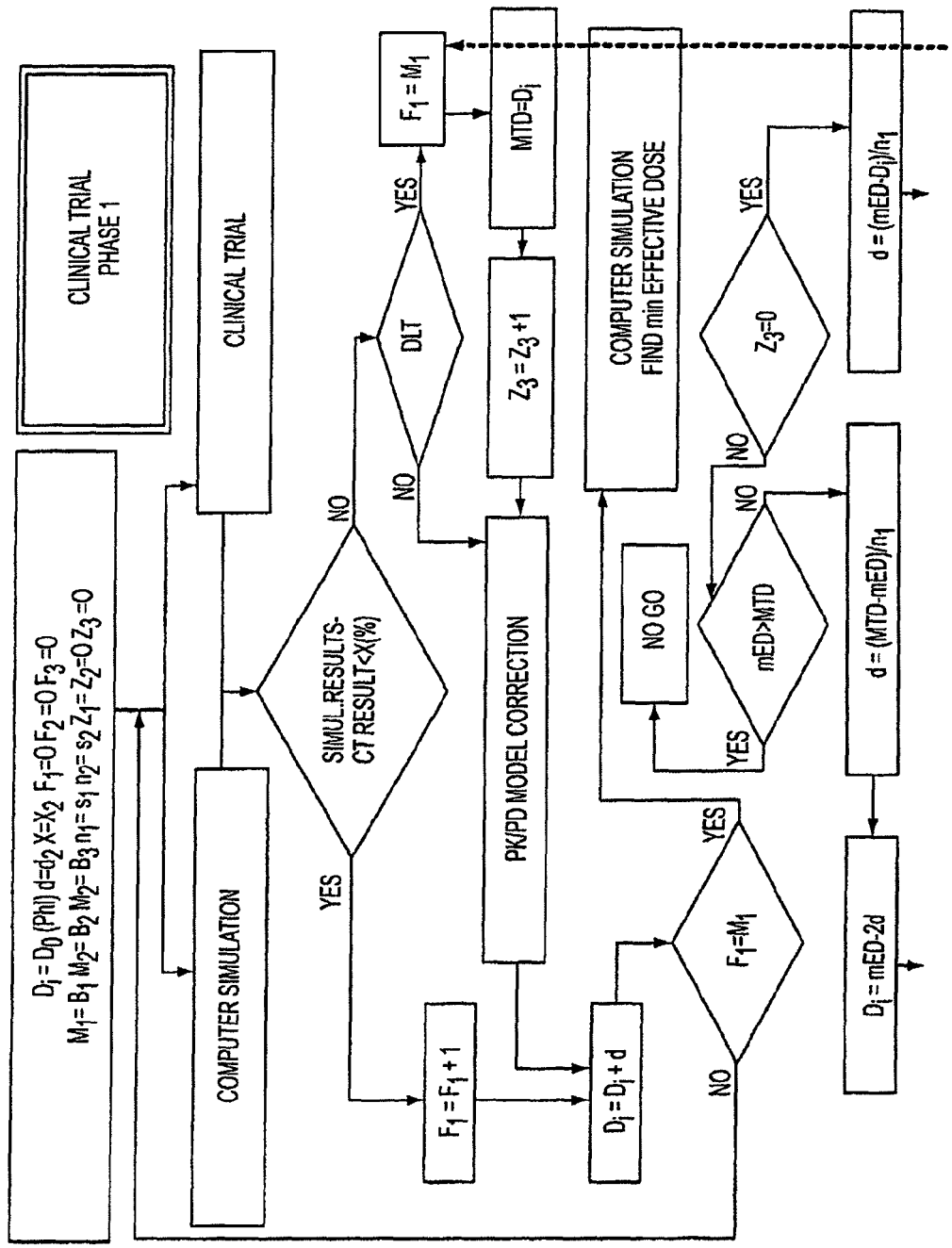

FIG. 22E shows one panel of an example implementation of the disclosed interactive trial design in the Phase I trial stage.

Figure 22F:
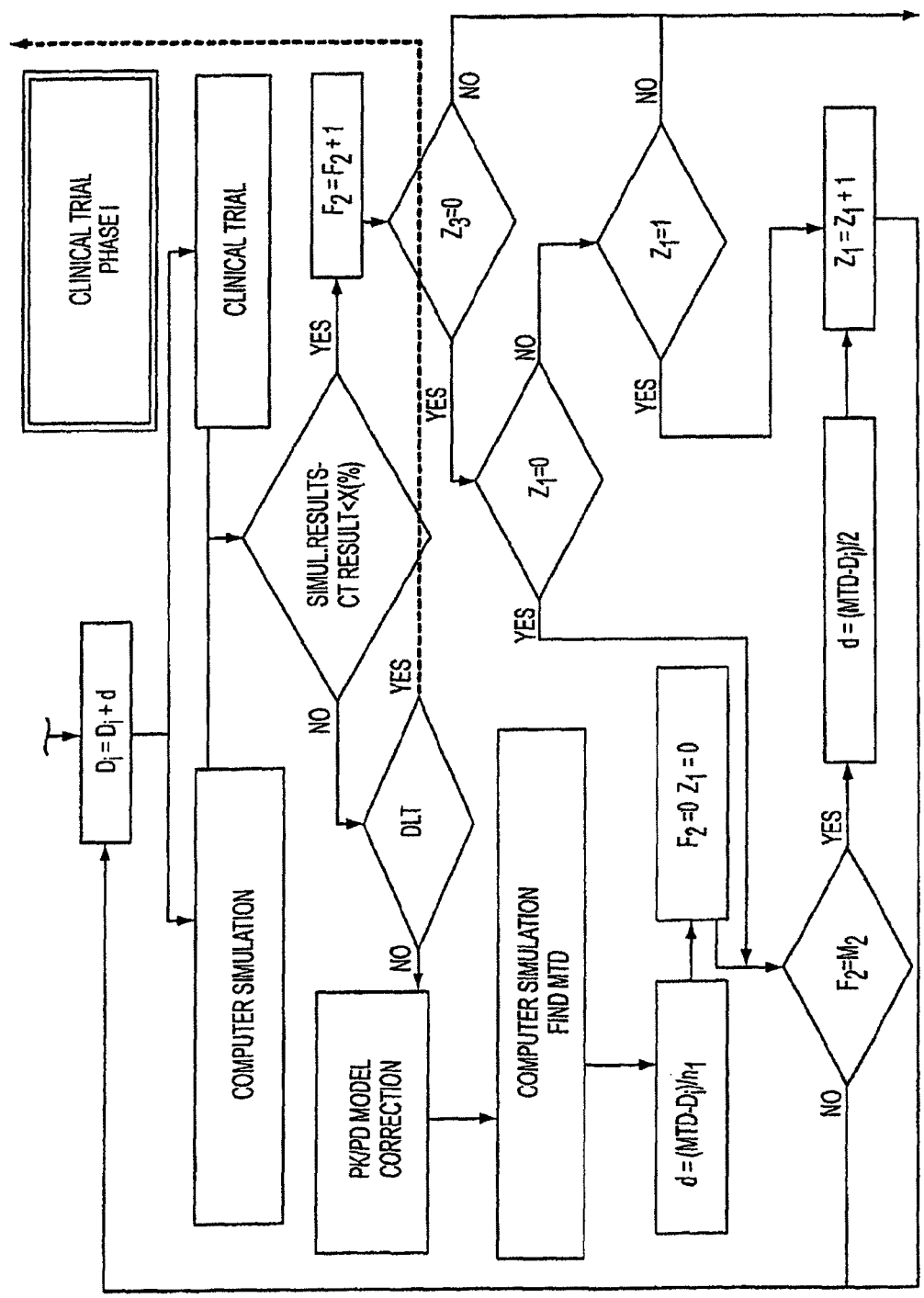

FIG. 22F shows one panel of an example implementation of the disclosed interactive trial design in the Phase I trial stage.

Figure 22G:
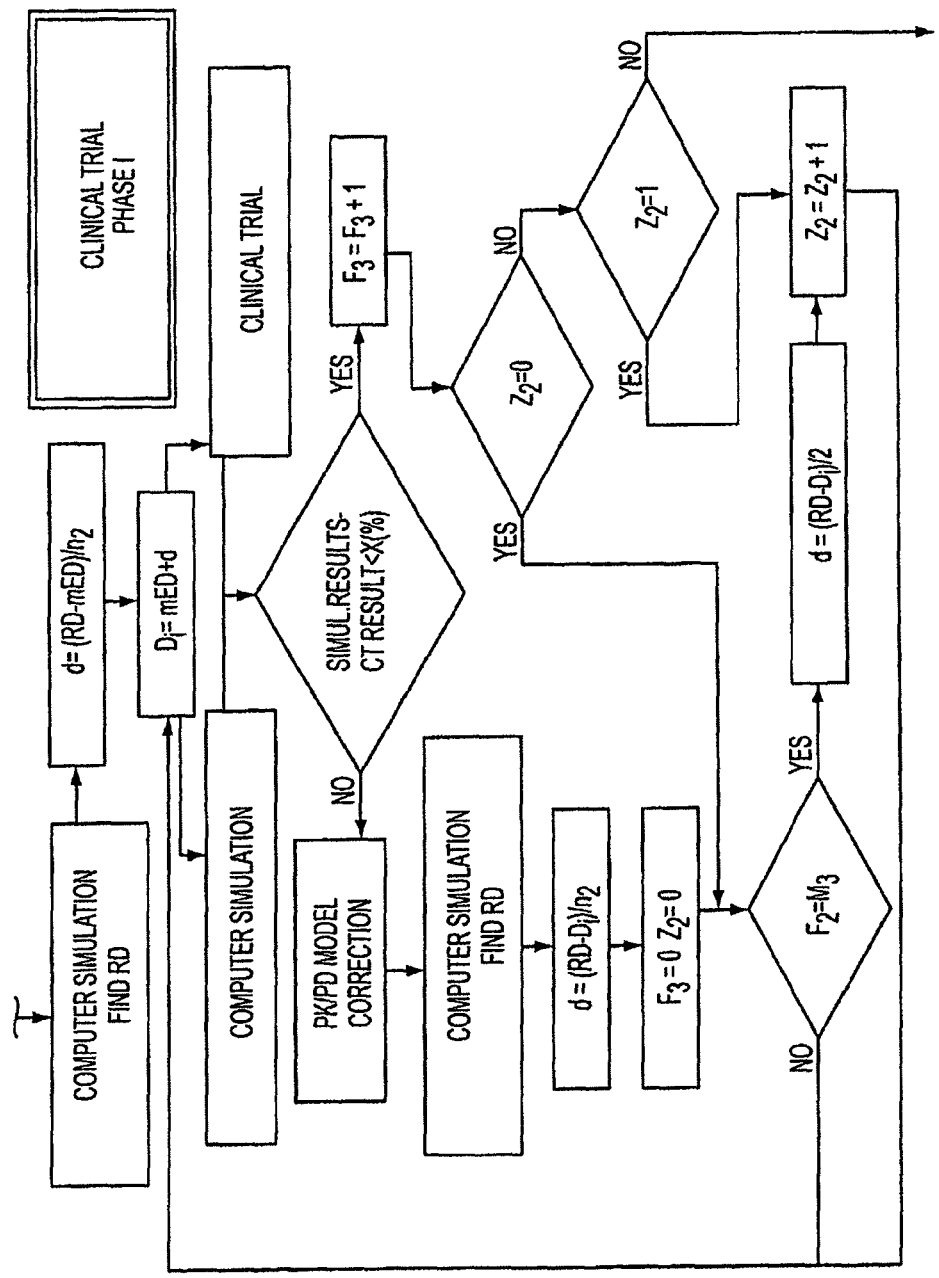

FIG. 22G shows one panel of an example implementation of the disclosed interactive trial design in the Phase I trial stage.

Figure 22H:
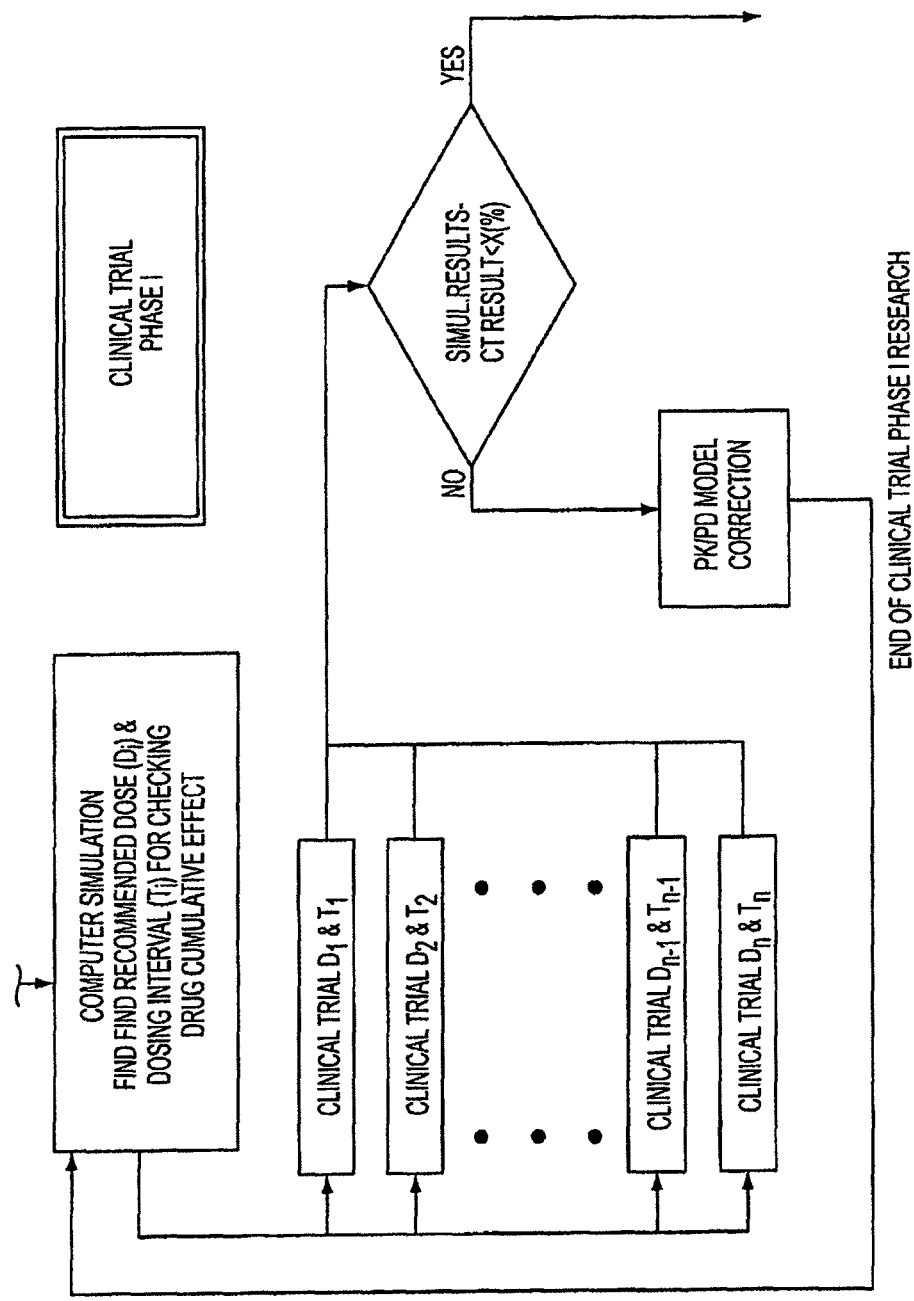

FIG. 22H shows one panel of an example implementation of the disclosed interactive trial design in the Phase I trial stage.

Figure 22I:
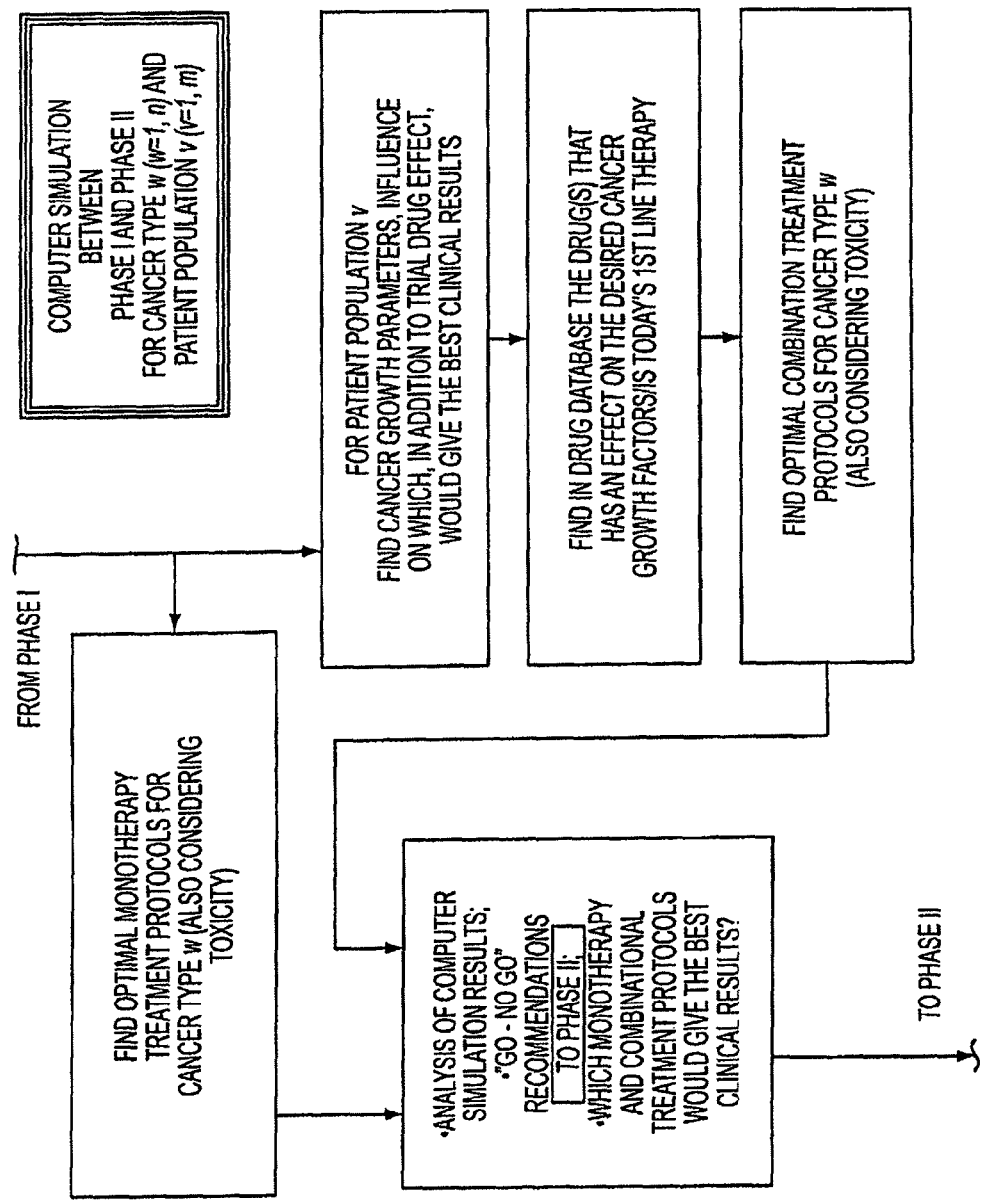

FIG. 22I shows an example of a computer simulation between Phase I and Phase II.

Figure 22J:
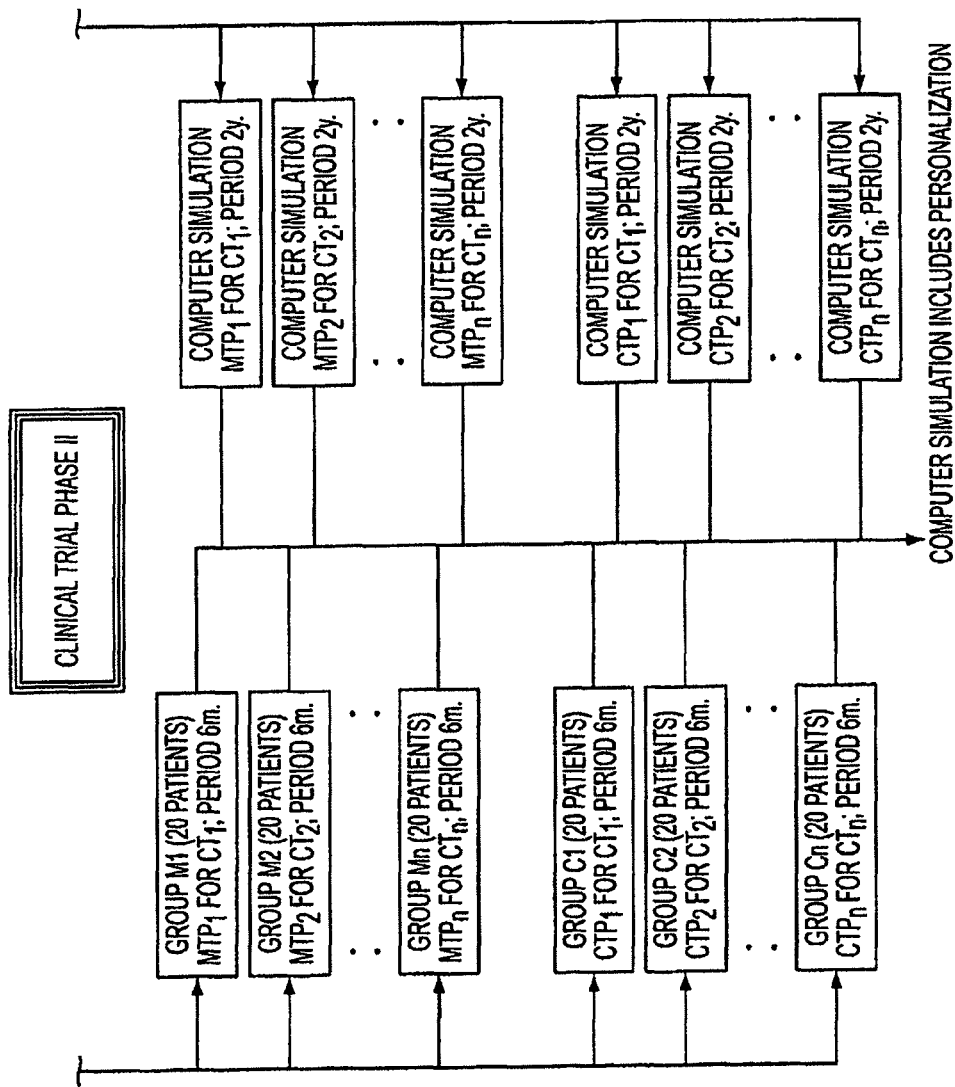

FIG. 22J shows one panel of an example implementation of the disclosed interactive trial design in the Phase II trial stage.

Figure 22K:
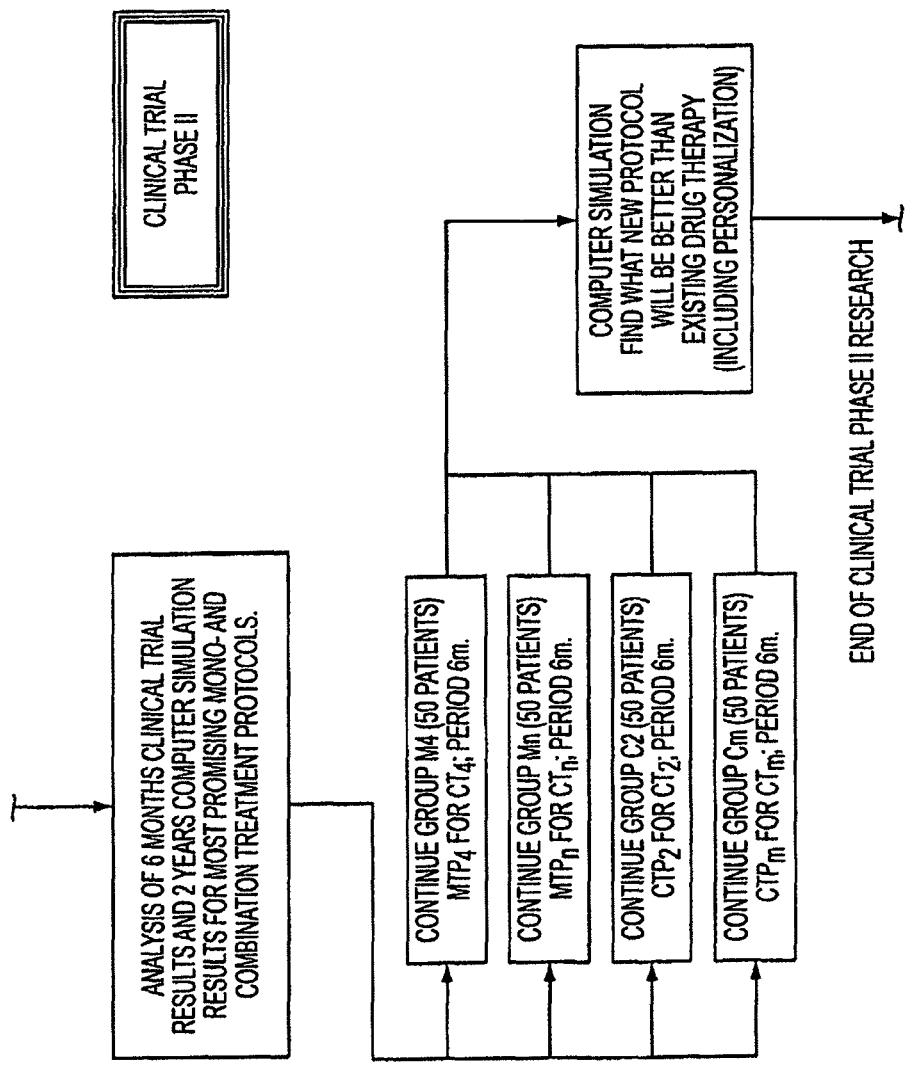

FIG. 22K shows one panel of an example implementation of the disclosed interactive trial design in the Phase II trial stage.

Figure 22L:
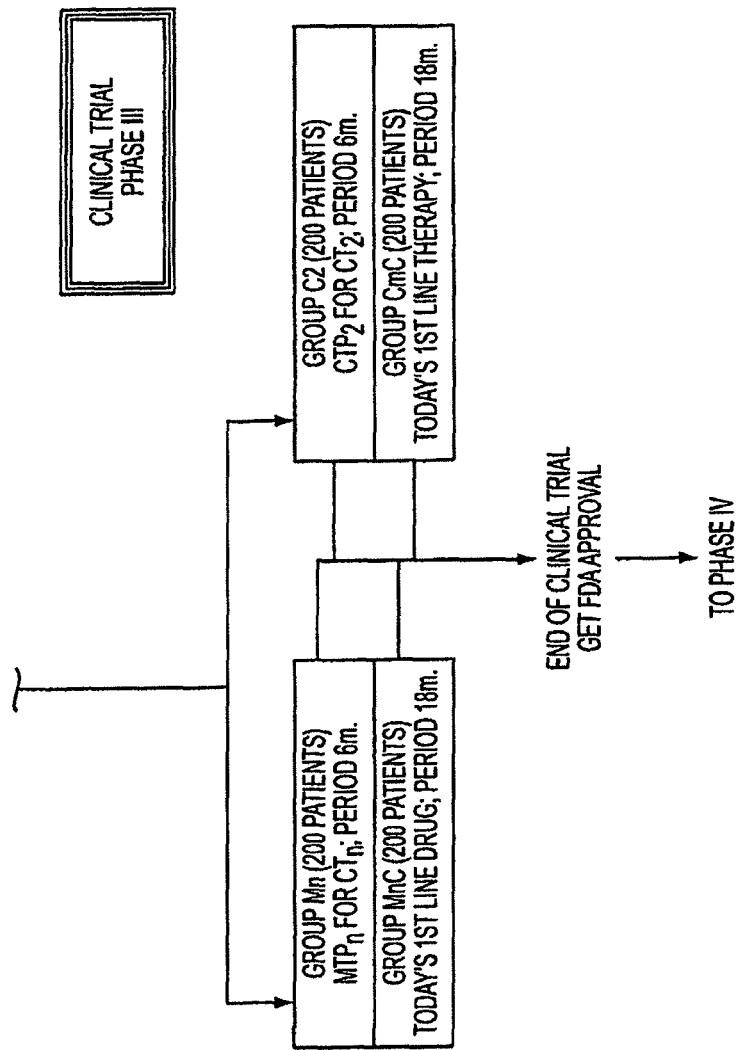

FIG. 22L shows one panel of an example implementation of the disclosed interactive trial design in the Phase III trial stage.

Figure 22M:
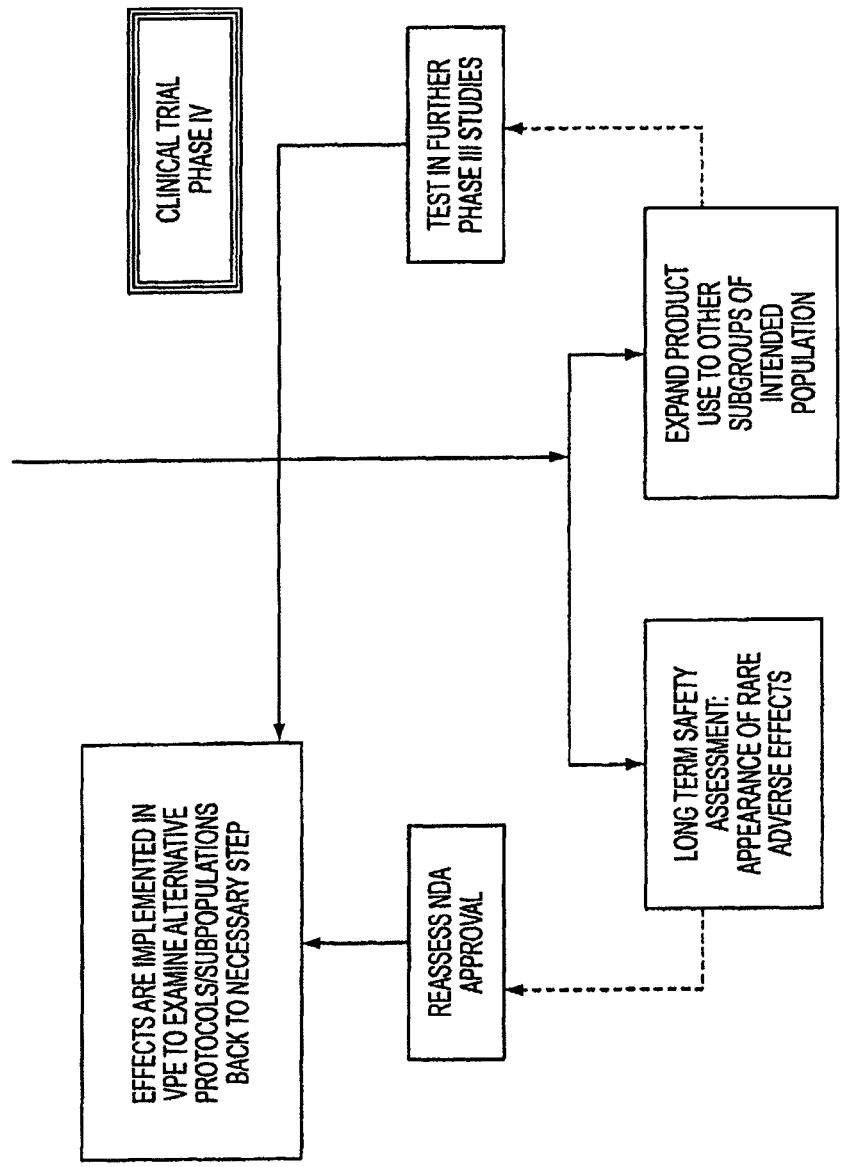

FIG. 22M shows one panel of an example implementation of the disclosed interactive trial design in the Phase IV trial stage.

Figure 23:
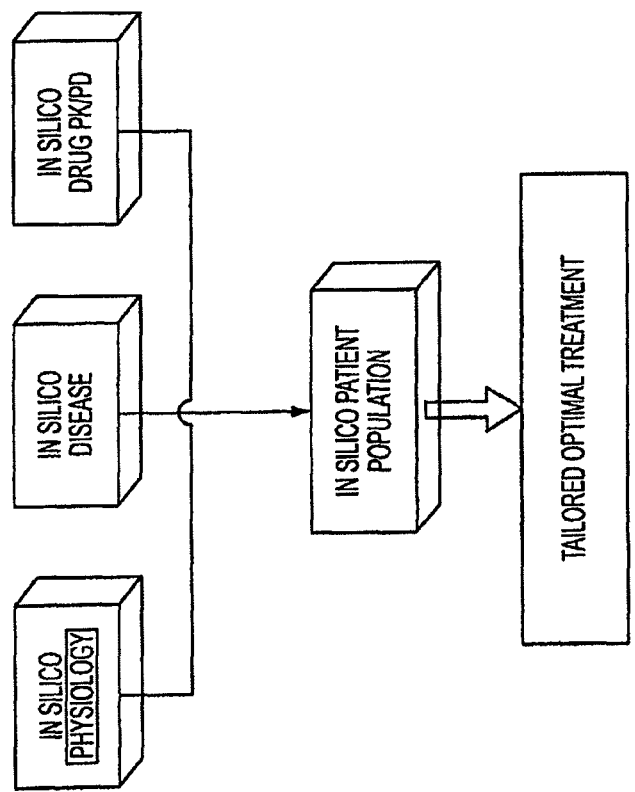

FIG. 23 shows an example of an overall framework for treatment optimization.

The panels from FIGS. 22A to 22M are connected to provide an overall diagram of implementation of the disclosed interactive trial design.

IV. DETAILED DESCRIPTION OF THE PRESENT INVENTION

The disclosed invention aims at providing a technique for purposing a new compound based on its preclinical and/or clinical available data. The technique aids drug developers in planning the next phase of clinical trials.

The invention also aims at providing a technique for repurposing a failed, approved or even marketed drug based on the available drug information.

Today, there exist elaborate and highly interdisciplinary and multidisciplinary methods, which can employ modern computing facilities for integrating the enormous body of relevant biological, medical, pharmacological and mathematical (dynamical) information into comprehensive systems for simulating different drug treatment scenarios. The techniques disclosed herein are based on more than two decades of biomathematical research in the area of disease control optimization [References 8-28]. Thus, mathematical algorithms have been developed, which simulate the dynamics of key biological, pathological and pharmacological processes in a patient undergoing drug treatment, either by monotherapy, or by combination of cytotoxic and/or cytostatic agents, and/or by growth-factors. This set of computerized mathematical models, in conjunction with advanced optimization algorithms have now yielded an in silico patient engine, having a range of applications designed to deliver optimal drug treatments for example, cancer and hematological disorders [e.g., References 38-39].

Disclosed herein are techniques for improving drug development, such as anticancer drug development, which employ such an in silico patient engine in drug development. The disclosed techniques enable the drug developer an ongoing dialogue, from pre-clinical phase through Phase-IV, for generating, fine-tuning and validating a reliable drug/disease/host model. Thus, relatively early during development, i.e., by the end of Phase-I, and no later than in mid-Phase-II, the model already contains the precise PK/PD drug parameters, to be implemented in the in silico patient simulations. At this stage numerous drug schedules (termed "infinite protocol space") are simulated for any desired indication, and proprietary optimization techniques are employed for selecting, among the vast number of simulation scenarios, those yielding best results according to the list of specifications set by the drug developer. In this way one identifies the most appropriate indications/monotherapy/combination treatments for the drug. At this early stage a "Go-NOGO" decision can be made.

Following the disclosed techniques, clinical trials may be rationally designed, which will be based upon a gradual improvement and zeroing-in on the best prediction-directed treatment schedules. It is important to stress that the disclosed technique carries little risk of yielding false predictions, since the algorithm has been designed so as to be continuously validated and improved by information derived in parallel from clinical trials.

An overall framework for treatment optimization is shown in FIG. 26. In the in silico Patient modules, mathematical algorithms for disease process, physiological processes & drug PK/PD are computerized. In the treatment Optimization Module—optimal treatments satisfying the user's (e.g., a Pharma company) specifications are predicted.

Given:
 1. Drug candidate (either under development, or whose development has been arrested, or marketed).
 2. Disease mathematical model.
 3. Mathematical computer models of physiological processes related to the disease.
 4. Parameters of one or more patient populations.
 5. Optimata's schedule optimization methods that are based on items 1-4 above.

For any chosen drug candidate the following are applied:
 1. Collect the pharmacological, preclinical and clinical trial results available for this drug.
 2. Construct the drug's pharmacokinetics (PK) and pharmacodynamics (PD) model, accounting for its observed effects.
 3. Simulate the drug's effects by calculating its PK and PD models, in conjunction with:
   A. one or more treatment schedules;
   B. one or more other drugs to be used in combination;
   C. one or more clinical indication;
   D. one or more patient population.

4. Evaluate drug effect by comparing simulation results with pre-specified criteria.

5. According to the simulation results, recommend the purposing/repurposing of the drug in question for a new indication and/or patient population and a treatment schedule in case its benefit for the new indication/patient population and treatment schedule proves to be superior to the benefits of existing drug therapies for the new indication/patient population.

The above teachings are applied to a preliminary phase for acquiring drug candidates and their relevant information. Drugs may be acquired by a screening process performed internally or may be provided by external drug developers interested in the technique.

The drugs may be found by searching many sources such as: private and public databases, scientific articles, pharmaceutical/biotechnology companies' proprietary information, medical institutions etc. It may either be acquired free of charge or through a cooperation agreement with a pharmaceutical company, an in-licensing agreement, full rights payment, or any commercial agreement.

Note that a compound in an early developmental stage which is a candidate for purposing is usually the proprietary information of the developing pharmaceutical company and is not available publicly. Thus, drug purposing candidates may also be obtained through a confidential agreement with the developing pharmaceutical company. It is usually initiated by the developing company due to difficulties and uncertainties raised in earlier stages of the trials].

Pre-Clinical Phase: Constructing the PK/PD Module

The pre-clinical phase of drug development is dedicated to retrieval of the drug's pharmacodynamics (PD) and pharmacokinetics (PK) in animals and to initializing human PD research. In this phase the computer model is adjusted to the drug under development, as is detailed below.

Based on the in vitro studies the drug PD module is constructed. Putative mechanisms of drug action are simulated, retrieving the most appropriate mechanism in the animal trials. From the results of the in vitro studies, the parameters of drug's effect on the different target tissues are empirically estimated and inputted into the module. These include the data of experiments using different tumor types, possibly in combination with another drug. Alternatively, the model here can simulate and comparatively estimate the efficacy of the treatment in combination with other known drugs, as well as the effect of the drug on different tumor types. In this way, pre-clinical research may be directed to the most effective avenues. The computer model is continuously fine-tuned, by "on-line" implementation in the in silico Patient, of the pre-clinical research results. Thus, the computer model interactively guides the empirical research to reveal the further necessary data.

Using animal studies, the PK module is adjusted to describe the PK of the given drug. The PD module, which until now was based on the in vitro data only, is adjusted to represent the in vivo results, and is supplemented with animal parameters for the functions of drug effect time series. This again, includes data on different tumor types and on the effects of combinations with other drugs. From animals treated by multiple doses, some data on cumulative effect can be obtained and implemented in the model.

The toxicity module is designed to include the qualitative and quantitative data on the side effects observed during the animal studies. In this way the module describing hemopoietic (hematopoietic) processes is provided with parameters of the drug effect on hemopoiesis (hematopoiesis), if observed in animals; other toxicities observed are described as a function of the drug time course. From animals treated by multiple doses, some data on cumulative toxicity may be obtained and implemented in the model as well.

At this stage the model already has the capacity to make approximate predictions on the administration of the drug to humans. Known inter-species differences in the effected tissue characteristics are taken into account when simulating the human PK model, in order to consider a reasonable dose range for Phase-I human studies. That procedure is expected to offer an improvement of the traditional LD10/10 initial dose for Phase-I trials, which is often too low to have any effect on the disease. That is to say that already in this stage, based on in vitro and in vivo data the model can be used for predicting the minimal dose within therapeutic range, i.e. the lowest dose, which has a rationale to be tested. It is possible at this point to use the model for predicting failure of the drugs with therapeutic doses too toxic to be tolerated.

FIG. 23A shows an example implementation of the phase of pre-clinical research where the pharma company checks the in vitro effect of the drug concentrations in human cells and in rodent cells. The idea is to escalate the dose until there is no additional effect.

FIG. 23B shows an example implementation of the phase of pre-clinical research where the pharma company checks the in vivo effect of the drug concentrations in rodents. The idea is to calculate the LD10(r) in rodents. Since the work in done in vivo, if animal death is observed, then at least the reason for the lethal effect can be partially clarified by calculating the effect of the drug administered at dose "i" in rodent or human toxicity tissue "k", i.e. ECDik(r/htox).

FIG. 23C shows an example implementation of the phase of pre-clinical research where the pharma company checks the in vivo effect of the drug concentrations in a nonrodent species. This is necessary in order to determine the initial dose of the drug (D0(PhI)) to begin Phase I clinical studies. The LD(nr) is calculated and compared to the LD10(r) and with this information D0(PhI) can be calculated.

FIG. 23D shows a summary table of all the data used to develop the PK/PD model. The shaded boxes in the table stand for concrete numbers.

Phase-I: Finalizing and Validating the PK/PD Module

During dose escalation testing in the Phase-I trials, the computer model (in silico patient) interacts with the trial, predicting the results for every step in the trial and, at termination of every step, is updated by implementing the observed effect and toxicity. In this way the computer model (in silico patient) is continuously validated and fine-tuned, to give better predictions in the next step. This could, possibly, save steps during dose escalation, which is necessary for obtaining the toxicity profile and an initial efficacy profile. During Phase-I trials, while using the intra-patient dose escalation method, the model is provided with data on cumulative effect and cumulative toxicity, if observed.

In this way, by the end of Phase-I, a fully verified in vivo human model is available, integrating all the existing data on PK and PD of the drug.

FIG. 23E shows an example implementation of steps in Phase I clinical research where the pharma company performs the clinical trial in parallel to computer simulations. The on-line cooperation between pharma's clinical trial and simulations can greatly facilitate the determination of the minimal effective dose (mED). If it is seen in simulation that mED>MTD (maximum tolerated dose), then an early NOGO decision can be made. At the same time, an early calculation of the dose elevation increment of the drug, d, can be made. In addition, in this stage, if the simulation results show that the clinical trial (CT) results>a chosen threshold (X), then the PK/PD model can be adjusted.

FIG. 23F shows an example implementation of steps in Phase I clinical research where the pharma company performs the clinical trial on the drug in parallel to computer simulations based on the disclosed techniques. Here, the MTD is determined and again, at this point, the algorithm allows an early determination of the dose escalation step, d. In addition, in this stage, if the simulation results show that the clinical trial (CT) results>a chosen threshold (X), then the PK/PD model can be adjusted.

FIG. 23G shows an example implementation of steps in Phase I clinical research where the pharma company performs the clinical trial on the drug in parallel to computer simulations based on the disclosed techniques. Here, the algorithm allows an early determination of the recommended dose (RD). Here again, the dose escalation step (d) is calculated. In addition, in this stage, if the simulation results show that the clinical trial (CT) results>a chosen threshold (X), then the PK/PD model can be adjusted.

At this point, the PK/PD model is completed. Also, MTD, mED and RD have already been calculated. Now, as shown in FIG. 5 many simulations are performed with different doses and dosing intervals. With these parallel virtual trials, the drug's cumulative effect is checked and again, if the simulation results show that the clinical trial (CT) results>a chosen threshold (X), then the PK/PD model can be adjusted as necessary.

Interim Stage Between Phase-I and Phase-II: Intensive Simulations of Short-Term Treatments Following Phase-I the model can yield reasonable, short-term predictions concerning the effects of definite drug administration schedules on disease progression for specific indications. This allows one to perform an exhaustive search in the protocol space (i.e., within all the treatment schedule possibilities), for those mono- and combination therapy schedules, which are expected to yield the highest response and lowest toxicity for any potential cancer type to be treated. This may help the drug developer to predict the most effective treatment schedule and the most promising indication, thus saving patient health, and time and costs of the drug's development.

FIG. 23I shows example implementations of steps in between Phase I and Phase II. At this point, many simulations are carried out with different cancer types in order to find the optimal protocol for different patient populations and different indications. The optimized result can then be compared with the first line therapy. At the end of this step, one can recommend which indications and patient populations to continue with to Phase III. Lastly, a GO-NOGO decision can be made at this point.

Phase-II and Phase-III: Focusing the Clinical Trials

At the onset of Phase-II trials and following the interim stage outlined in section 3, a few proposed treatment schedules for the selected indication(s) are applied in short pilot trials testing a relatively small number of patients. After the first results are obtained (supposedly 6 months on average), the model should be adjusted by implementing the new data on the observed effects (including that indicated by surrogate markers).

Subsequently, a new set of intensive simulations is carried out, predicting disease progression during an extended period of up to two years, and predicting which of the schedules, tested in short-term trials, are expected to yield the best results in the long-run (changes can be made to the schedules in accordance with the model predictions). At this stage the predicted effect for each selected schedule is compared with that of existing therapies for the same indications. The model allows personalization for the patients involved in the study, based on the results obtained after the first 6 months, to yield more precise predictions.

At this stage, the model can predict failure, that is, recommend a NOGO decision, for the drugs that are incapable of demonstrating benefit over the existing therapies. The schedule(s) predicted to carry the most significant benefit over the existing treatments are selected for further testing in Phase-III. After the efficacy and safety profile of the selected schedule(s) is confirmed in further Phase-II trials (for another 6 months), the selected schedules should be further tested in extended group of patients as Phase-III trials.

FIG. 23J shows an example implementation of steps of Phase II clinical research where the pharma company performs a series of small clinical trials in parallel with small numbers of patients. Recommendations from the model are tested in these trials. From this group of clinical trials, the interim results at 6 months are analyzed and long term computer simulations (simulated for a period of 2 years) are performed. From all of these small parallel clinical trials, the most promising are chosen to continue for another 6 months in parallel.

As shown in FIG. 23K Phase II is continued with the most promising trials in parallel for another 6 months. Again, there is another round of data analysis, long term simulations and finally, the optimal protocol is chosen to continue to Phase III studies.

Further, as shown in FIG. 23L Phase III studies are carried out in a large number of patients and compare the test drug to standard therapy. The disclosed techniques thereby streamline the clinical development process by combining Phase II and III and efficiently contribute to an expedited FDA submission.

Finally, as shown in FIG. 23M, Phase IV studies are carried out after market approval and long term safety assessment and subpopulation analyses are carried out in the virtual patient engine (VPE). If rare side effects or unexpected drug interactions are found in certain subpopulations, then the disclosed technique can recommend to which step the developer should go back to in order to improve drug performance.

Figure 19:
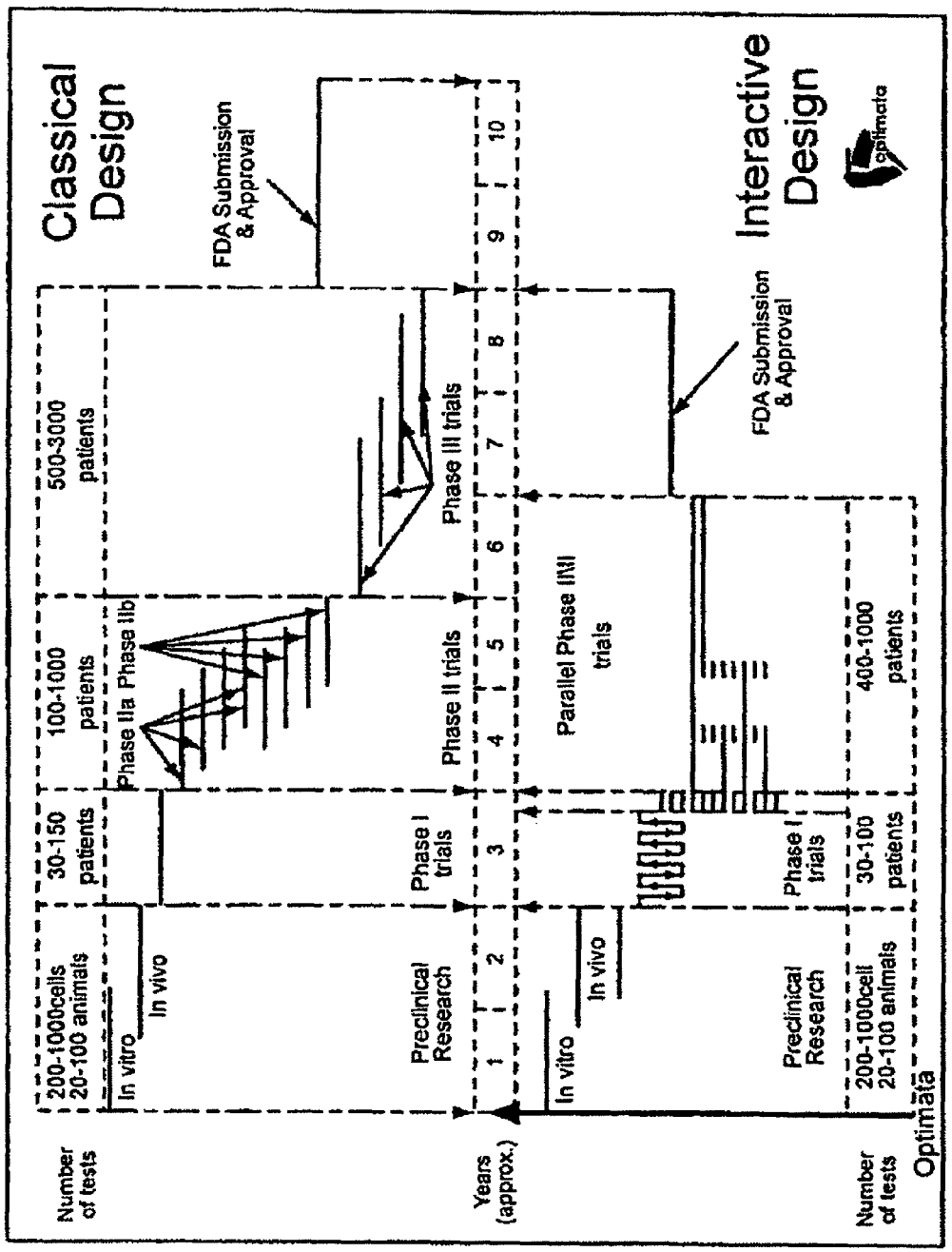
FIG. 19 shows duration and number of patients (averages) to be engaged in the Interactive Clinical Trial Design as compared to those in the classical design.
Figure 20A:
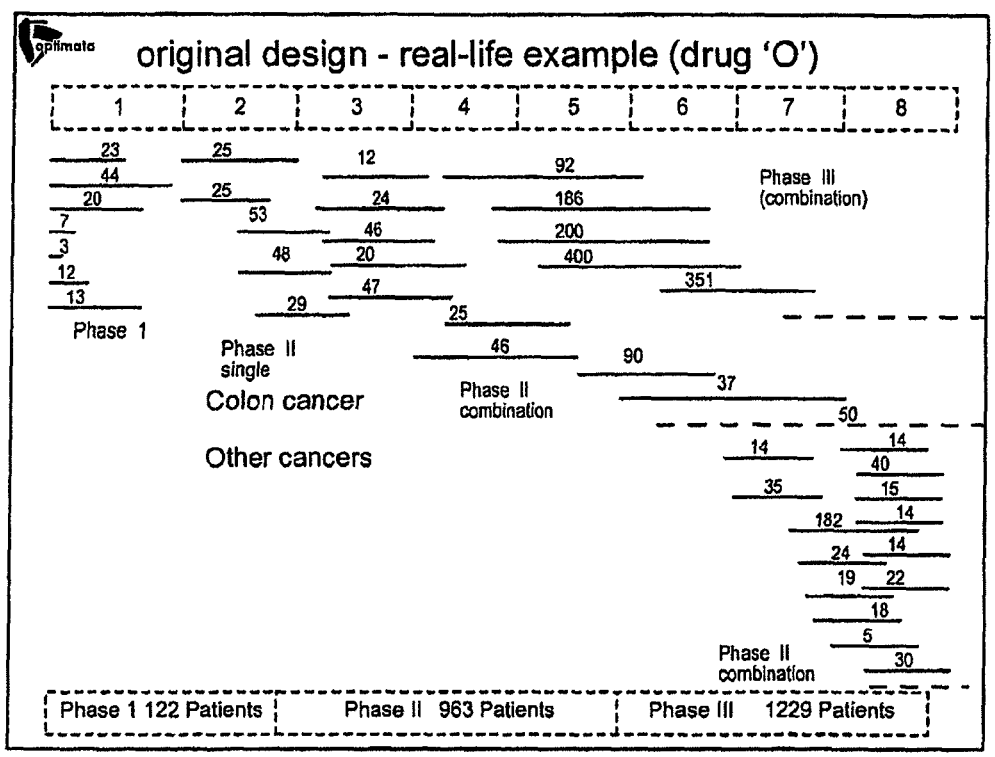
FIG. 20A shows a classical clinical trial protocol for drug "O" as compared to an example implementation of the disclosed interactive clinical design protocol based on stages of implementing an example implementation of the disclosed teachings.
Figure 20B:
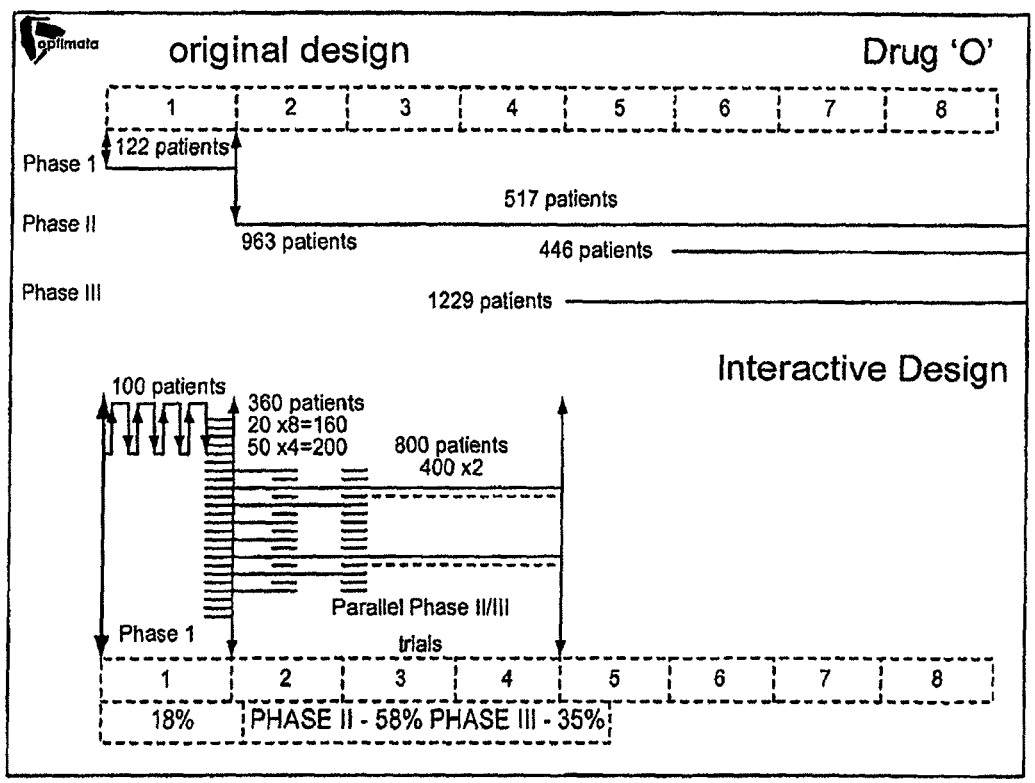
Figure 20C:
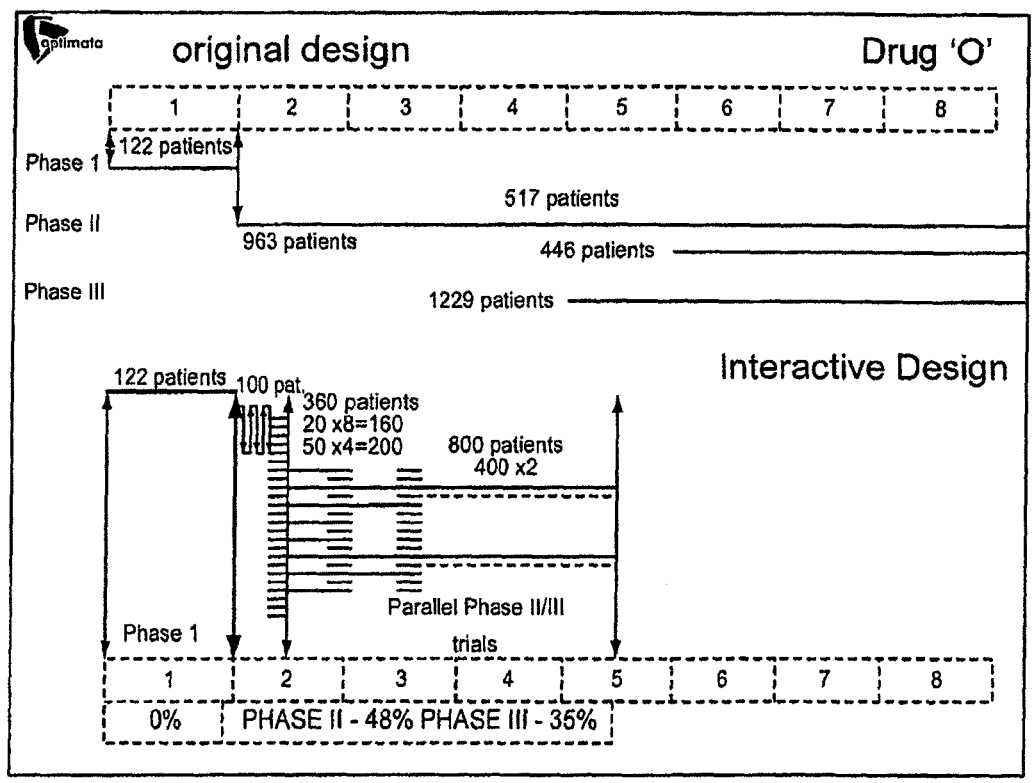
Figure 20D:
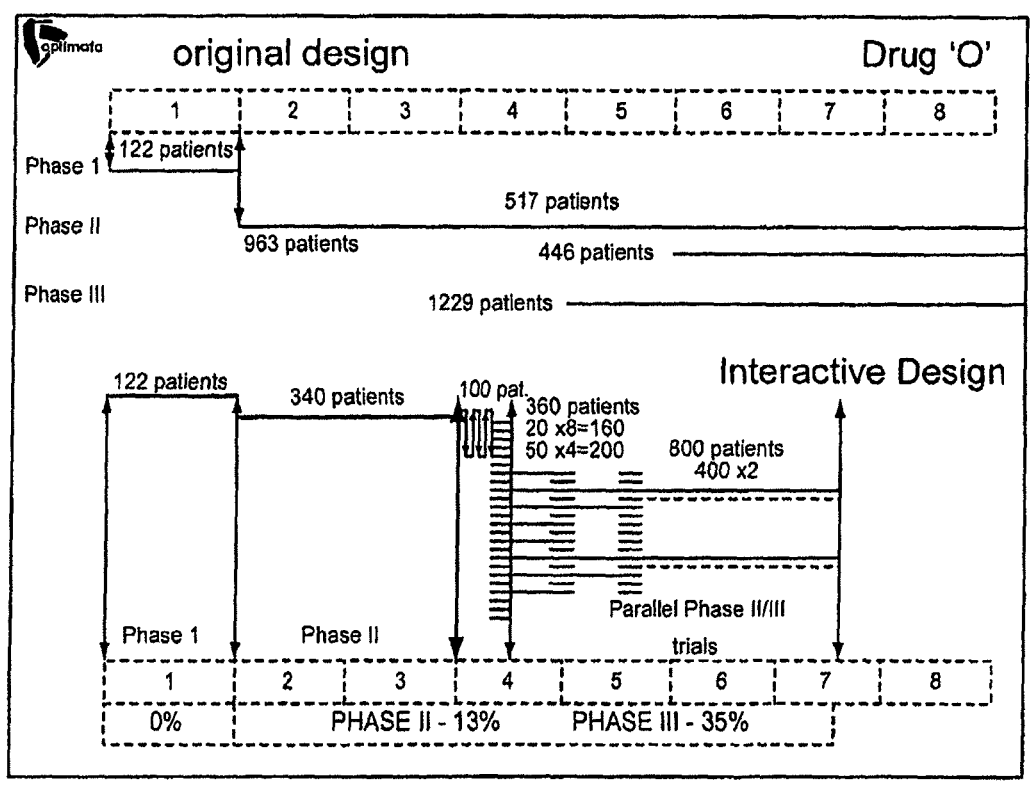
Figure 20E:
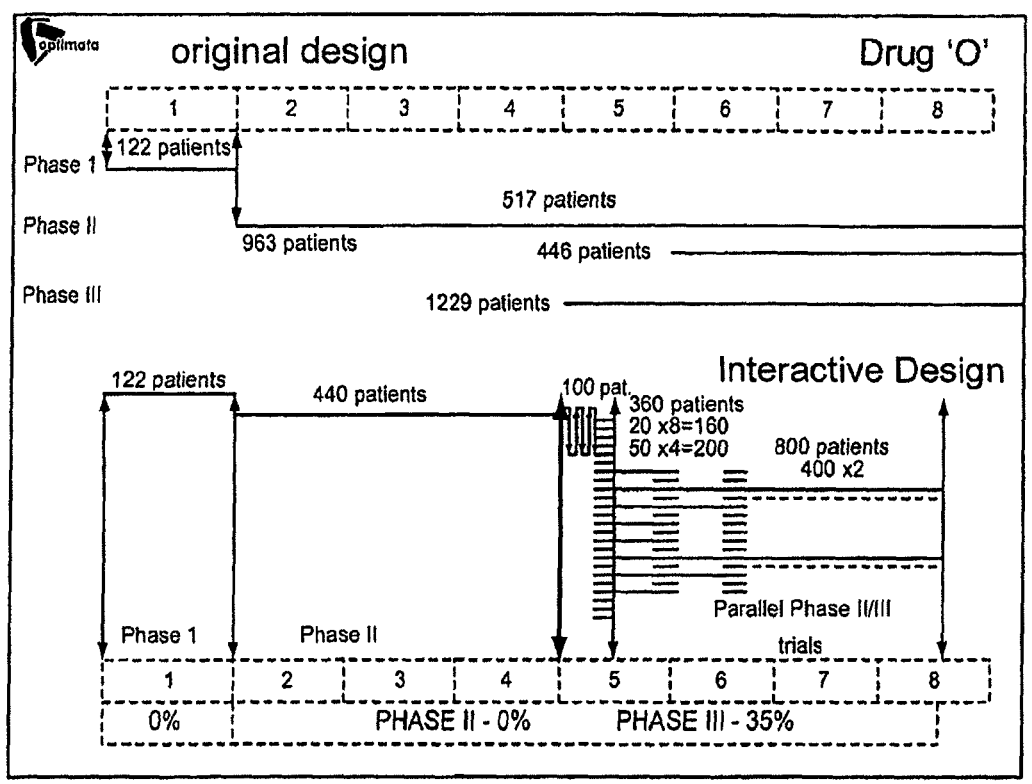

The example implementation of the interactive clinical trial design was compared to a classical clinical trial design of anti-cancer drugs (denoted original). FIG. 19 illustrates the average differences in the number of patients expected to be engaged in the clinical trials designed according to each of the two methods.

One can notice in this figure a significant predicted saving in time and in the number of patients, which the technique of interactive clinical trials design offers. FIGS. 20A-20E schematically present the results of the theoretical comparison between the classical design in the development of a test drug "O", currently in Phase II-III in one of the big Pharma companies and the design of the same drug under the interactive clinical trials technique; the differences (in percentage) in the number of patients and the total duration of drug development are noted at the bottom of FIGS. 20B-20E.

Interactive Clinical Trial Design as Compared to the Adaptive Trial Design Method "Adaptive designs are dynamic". They are based on the assumptions of Bayesian statistics (in contrast to the classical design, which is based on frequentists assumptions). Adaptive design trials suggest an improvement to the classical design, as they offer ability to stop trials relatively early, drop or add treatment groups, change group proportions or shift seamlessly into a later phase, etc. These models aid in planning trials by predicting the probability distribution of trial outcomes conditional on current knowledge and assumption, and thus evaluating the ability of the trial to support a certain decision. These models rely upon prior probability distribution (e.g. FIG. 21) [40-42].

By comparing FIG. 21 to FIG. 19, one can immediately notice the main differences between the two methods: (a) the point of influence of the Interactive Design can be as early as the Pre-clinical stage, whereas the point of influence of the Adaptive Design begins only in Phase-II; (b) moreover, while the first and potentially most important decision-making impact of the Interactive Trial Design takes effect already at the end of Phase-I, the Adaptive Trial design's impact can be effectuated only towards the end of Phase-III. The reason for these differences lies in the significant distinction between the tools employed by each of the designs. A major asset offered by the disclosed technique is its predictive power, rather than the improved data analysis methods, offered by the Adaptive Design. In other words, the disclosed design is primarily prospective, integrating all the available biological, medical, pharmacological, theoretical and clinical information. In contrast, Adaptive design is primarily retrospective, integrating statistical methods with the information from the clinical trials.

Other modifications and variations to the invention will be apparent to those skilled in the art from the foregoing disclosure and teachings. Thus, while only certain embodiments of the invention have been specifically described herein, it will be apparent that numerous modifications may be made thereto without departing from the spirit and scope of the invention.

FIG. 24 shows an example of the implementation of the disclosed techniques. It should be noted that the scope of the disclosed technique is not limited specifically to this example which is merely illustrative and exemplary in nature of the claimed invention.

Figure 4:
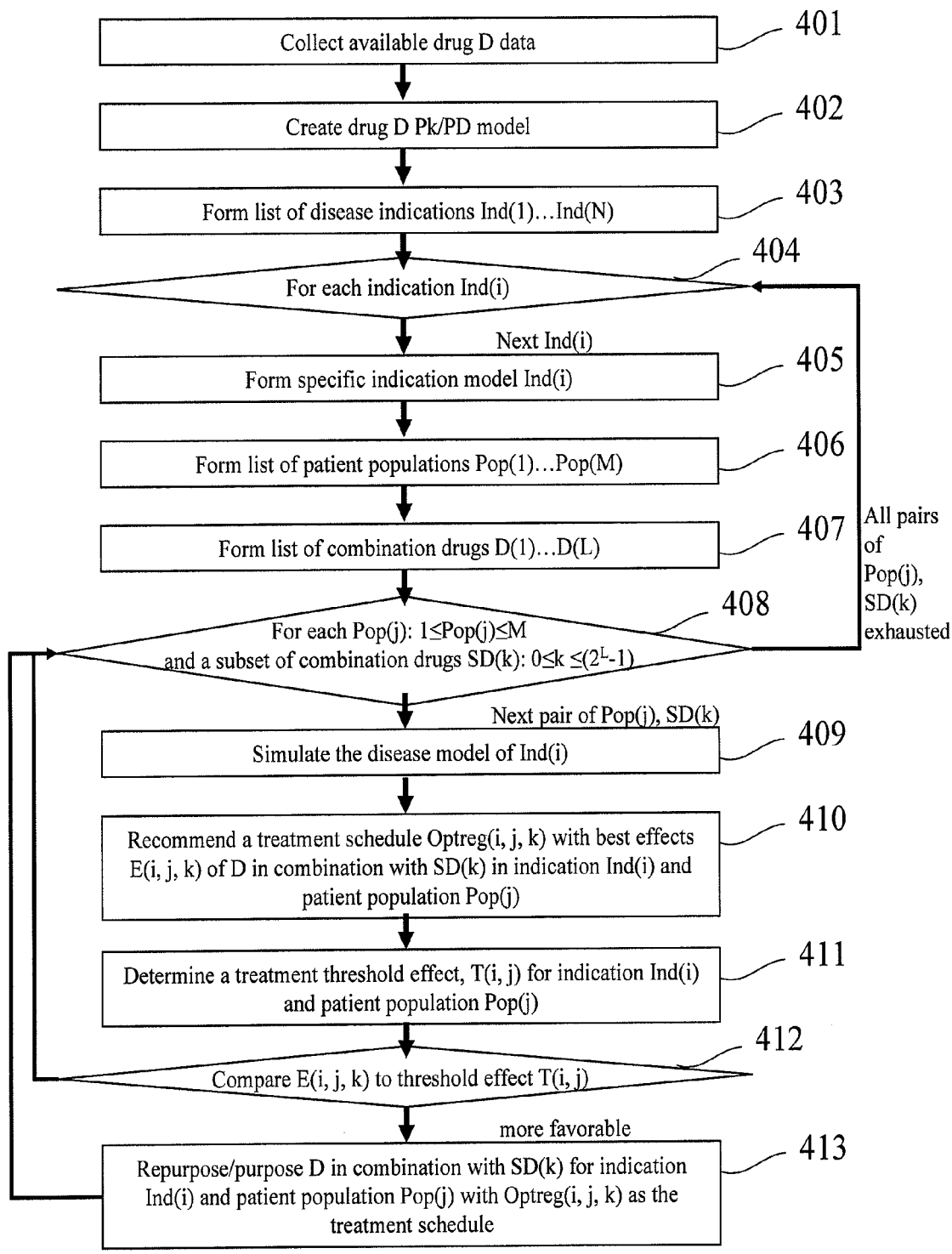
FIG. 4 shows a flowchart depicting an exemplary implementation embodying the disclosed teachings.

More specifically, as shown in FIG. 4, given a drug candidate D the repurposing/purposing of D involve applying the steps as described below:

1. Collect all the preclinical and clinical trials results already available for this drug D (step 401).
2. Create the drug pharmacokinetics (PK) and pharmacodynamics (PD) model, accounting for its observed effects (step 402).
3. Form a list of relevant disease clinical indications: $Ind_{\{1\}} \ldots Ind_{\{N\}}$ (step 403).
4. For each indication $Ind_{\{i\}}$, $1 \leq i \leq N$ (step 404):
   4.1. Create $Ind_{\{i\}}$ disease indication model, incorporating the drug effects on disease progression (step 405).
   4.2. Form a list of patient populations $Pop_{\{1\}} \ldots Pop_{\{M\}}$ with relevance to Drug D and clinical indication $Ind_{\{i\}}$ (step 406).
   4.3. Form a list of drugs $D_{\{1\}} \ldots D_{\{L\}}$ potential for combination therapy with drug D (step 407).
   4.4. For each patient population group $Pop_{\{j\}}$:$1 \leq j \leq M$ and a subset of combination drugs $SD_{\{k\}}$:$0 \leq k \leq (2^L-1)$ (subset can be empty indicating mono-therapy), do the following (step 408):
      4.4.1. Simulate the disease model of indication $Ind_{\{i\}}$ in conjunction with (step 409):
         1. drug D computer model
         2. patient population $Pop_{\{j\}}$ parameters
         3. models of drugs in the subset $SD_{\{k\}}$ of combination drugs
         4. toxicity model (optional)
      4.4.2. Recommend a treatment schedule Optreg(i, j, k), which is predicted by the simulations to carry the best effects, E(i, j, k), of the drug D in combination with drugs in $SD_{\{k\}}$ on the selected indication, $Ind_{\{i\}}$ and patient population, $Pop_{\{j\}}$ (step 410).

The optimality of the effects is determined by the user's predetermined criteria. For instance, the optimality of the effects may be the best effects on disease progression, minimal toxicity, or a combination thereof or any other predetermined desired effect selected by the user.

4.4.3. Determine a treatment threshold effect T(i, j), for $Ind_{\{i\}}$ in $Pop_{\{j\}}$. In the event a treatment for $Ind_{\{i\}}$ in $Pop_{\{j\}}$ exists the threshold may be decided according to the effect of the existing treatments (step 411).
      4.4.4. Compare the optimal effect E(i, j, k) of the drug treatment to the predetermined threshold effect, T(i, j) (step 412).
      4.4.5. If E(i, j, k) is more favorable than T(i, j), recommend the repurposing/purposing of the drug D for indication $Ind_{\{i\}}$, patient population $Pop_{\{j\}}$ in combination with $SD_{\{k\}}$ drugs and Optreg(i, j, k) as the treatment schedule (step 413).

Figure 18:
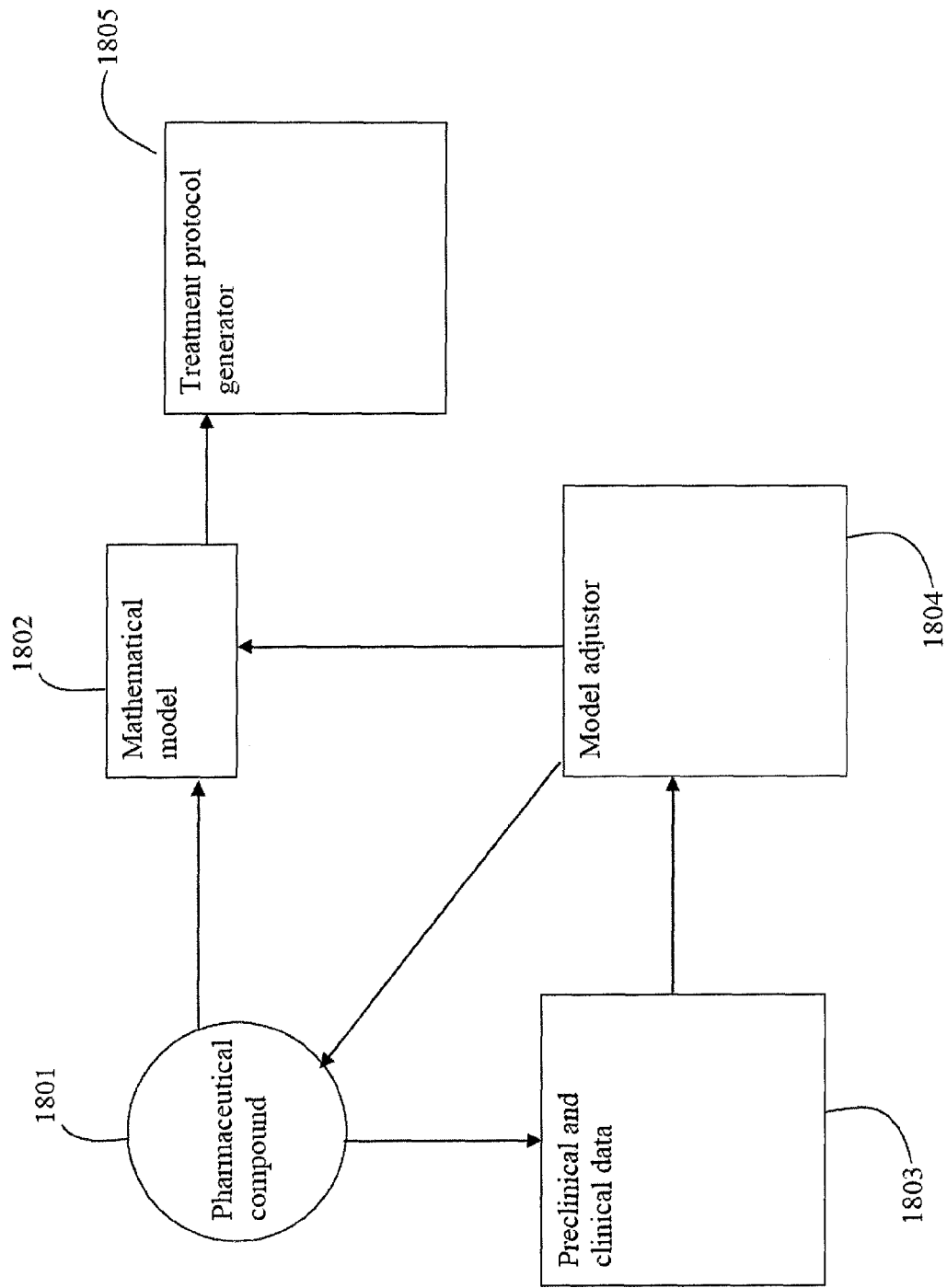
FIG. 18 shows an exemplary embodiment of a system embodying the disclosed teachings.

FIG. 18 shows an exemplary embodiment of system for repurposing a pharmaceutical compound embodying aspects of the disclosed teachings. Item 1801 is a pharmaceutical compound that has failed in clinical development or an approved drug. A mathematical model 1802 describes the physiological processes related to a disease and the effect of the pharmaceutical compound on the disease. A model adjustor 1804, which is not an obligatory component of the system, adjusts the model based upon information from preclinical or clinical trials 1803. A treatment protocol generator 1805 that suggests a new treatment protocol to salvage the failed compound or new way to use an approved drug. It should be clear that this suggestion can be conveyed to a user as a display/output from a computer.

It should be further clear that the systems and methods (techniques) can be implemented on a general purpose computer as a stand alone machine, a computer (or computers) that form part of a network, or remotely using the internet and a combination thereof. It can be implemented in hardware, software or in a combination thereof A computer program product that includes computer implemented media that has a set of instructions that implement the above systems and methods (techniques) is also a part of the invention. The media can be RAM, ROM, flash memory, hard disks, floppies, CDs or any other tangible media that can store instructions that can be implemented on a computer.

EXAMPLES

Example A

Purposing Compound Under Development

In the example below, the present invention is used for purposing an anticancer drug under development in collaboration with the developing pharmaceutical company.

The method submitted here was used for two clinical indications (A and B), considered by the pharmaceutical company for phase II clinical trials. Optimata's recommended optimal treatment schedule for each indication was weighed against several treatment schedules such as the gold standard treatment for that indication, and the pharmaceutical company's suggested treatment schedule for each indication. The response to each of these treatment schedules was predicted, and a recommendation was provided to the pharmaceutical company for the treatment with the best predicted response.

For indication A, it was predicted (by the simulations, step 4.4.1) that the effective therapeutic window (a dose range for which the drug is effective) for the pharmaceutical company's suggested treatment schedule was above the dose limiting toxicity (an allowed dose limit obtained from phase I, above which the drug is toxic). The best schedule predicted by Optimata shown to provide no further superior results over the standard of care for indication A. Thus, a "No Go" recommendation was provided, that is, not to purpose the drug for indication A. This recommendation was taken into consideration by the pharmaceutical company. For the other indication (denoted by indication B in the figures discussed below), a new schedule was predicted providing optimal effects (40% of patients were predicted to have a stable disease), and that the response of patients with indication B to the drug in question would be better than the response to the gold standard treatment for indication B (where 18% of patients are predicted to have a stable disease or partial response). As a consequence, the drug was purposed for indication B for the Phase II clinical trials.

The above example is illustrated in the figures below as follows:

FIG. 5 demonstrates the predicted response in both indications for the drug schedule originally suggested by the pharmaceutical company.

Figure 6:
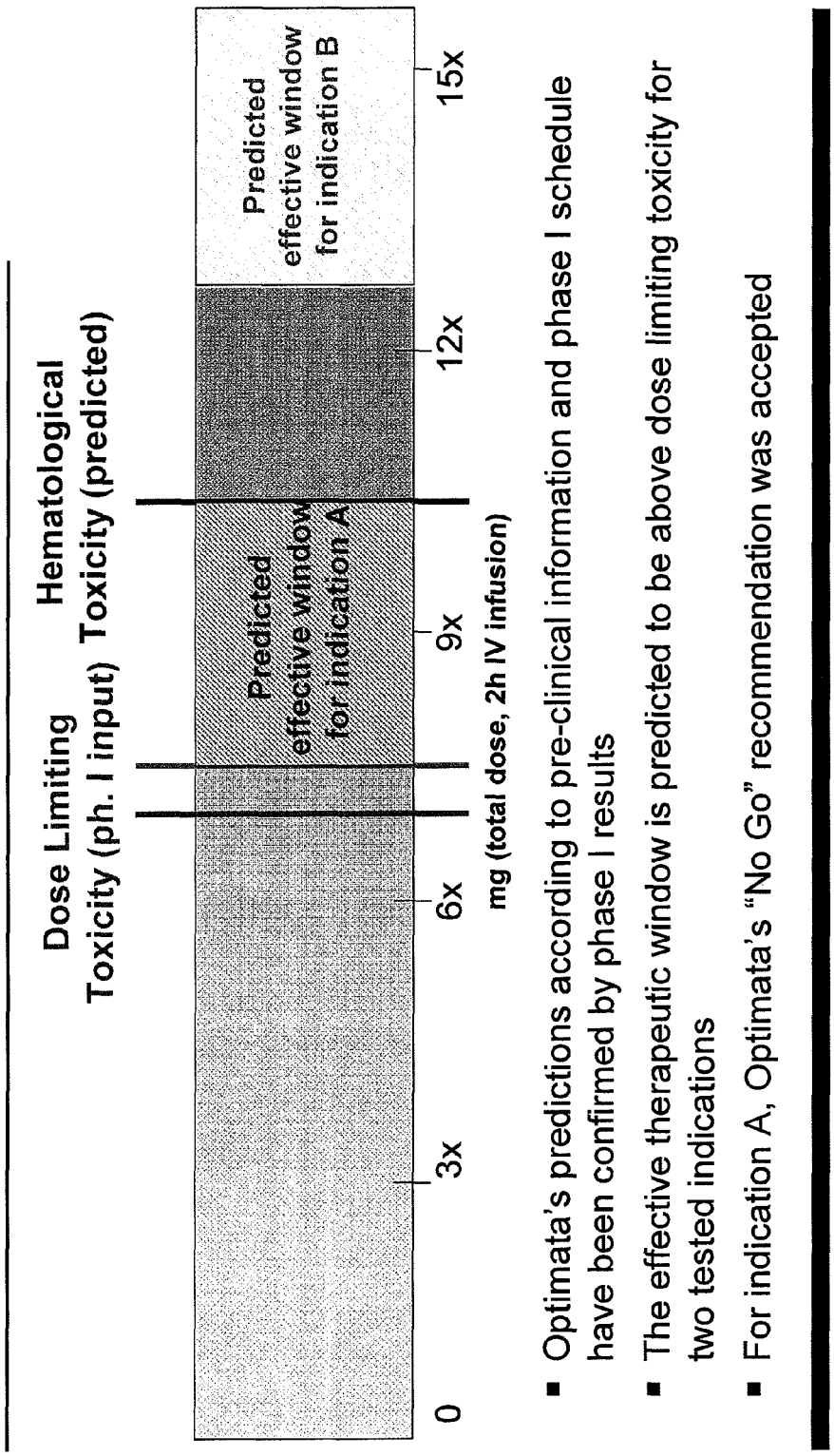
FIG. 6 shows the predicted effective therapeutic window for both indications with suggested phase I schedule and dose limiting toxicity obtained from phase I.

FIG. 6 demonstrates that the predicted effective therapeutic window for both indications with phase I schedule is above dose limiting toxicity.

Figure 7:
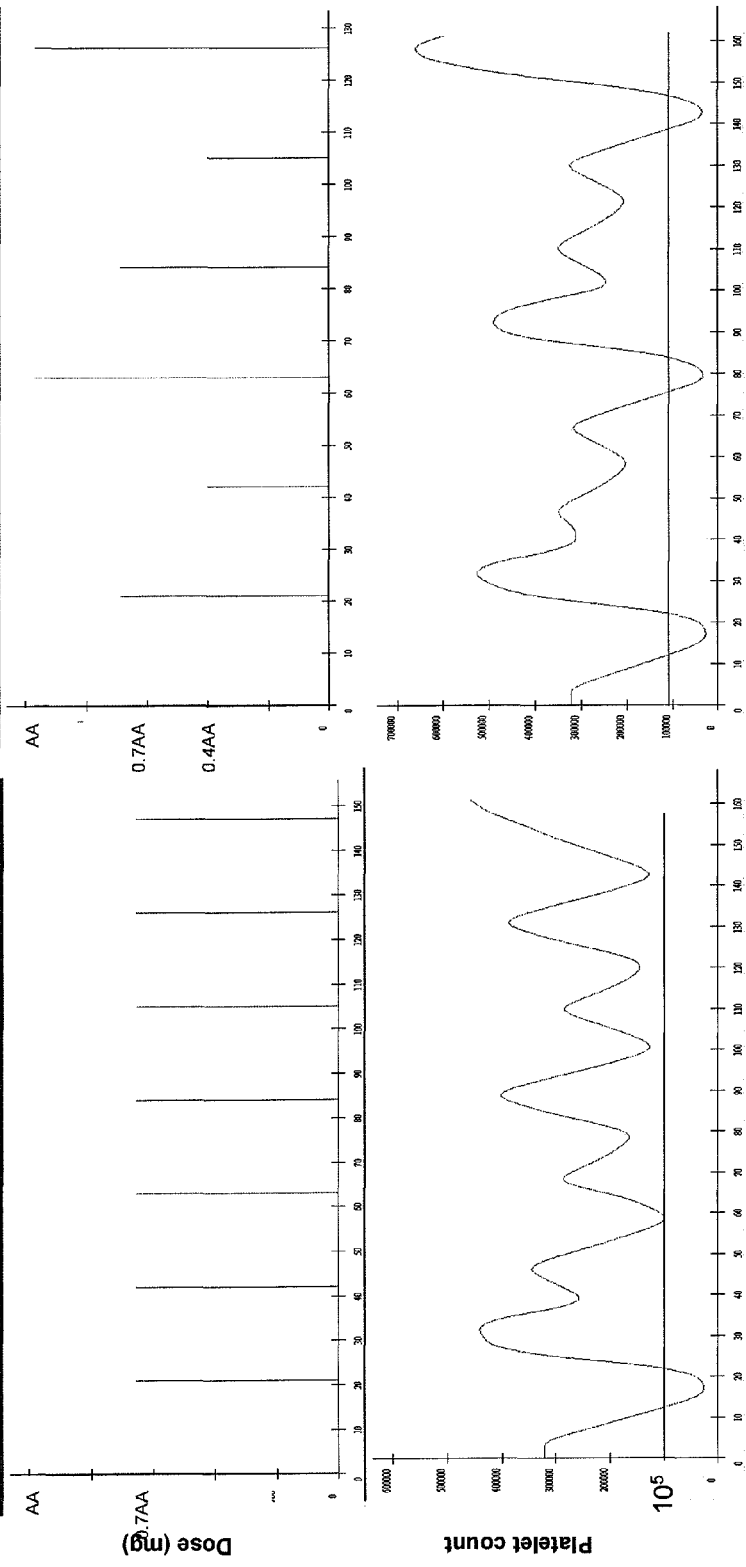
FIG. 7 shows the computer simulated platelet counts as a function of time for two different drug schedules; the red line marks the upper limit platelet count for thrombocytopenia grade III.

FIG. 7 shows the two treatment schedules for indication B, the one originally suggested by the pharmaceutical company and the one recommended by Optimata. Each schedule is described in a graph indicating the dosage given over different time points. In addition, the level of toxicity for both schedules is presented in a graph of platelet counts over time where low platelet count is toxic.

Figure 8:
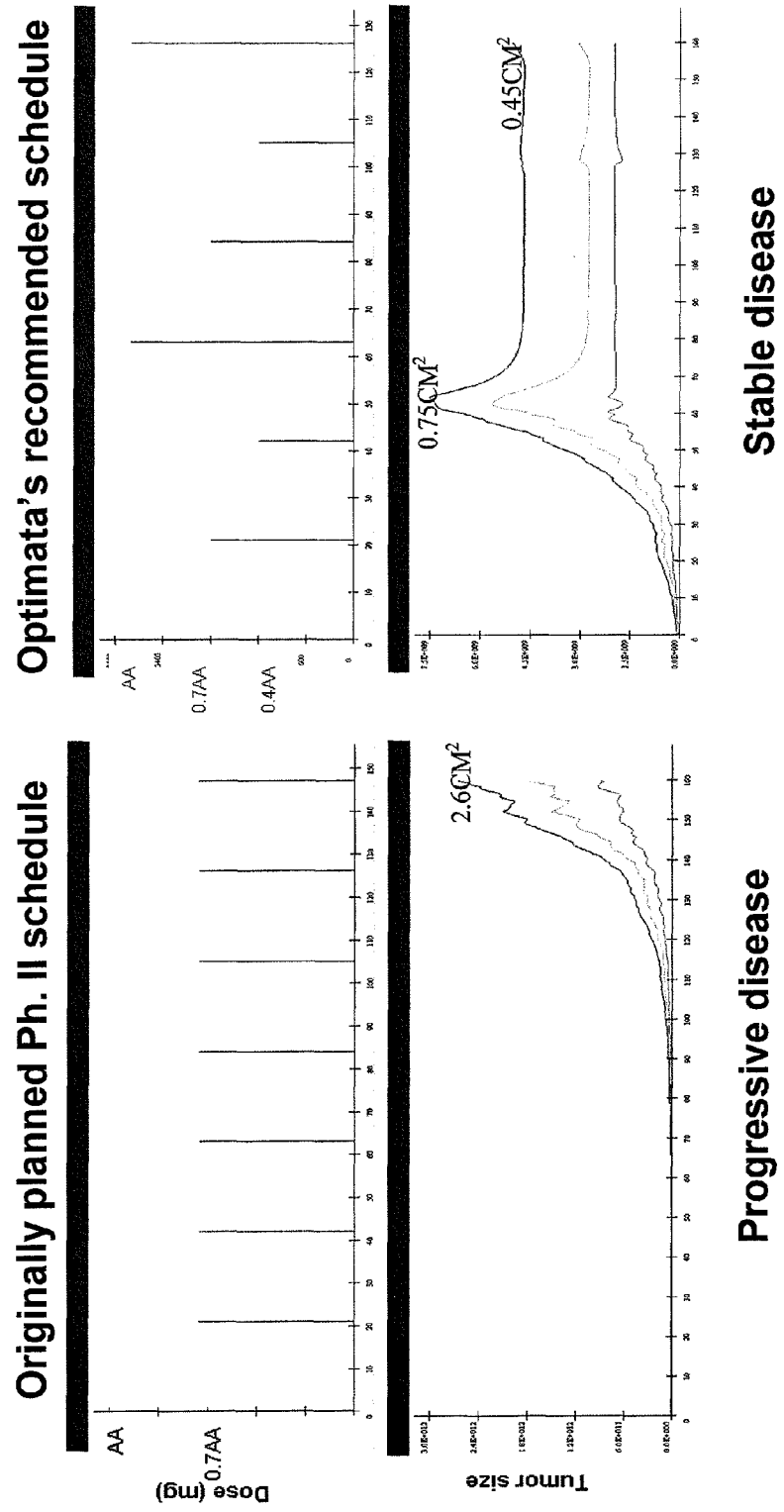
FIG. 8 shows tumor size simulation results for indication B for two drug schedules. One demonstrates a stable disease tumor growth pattern while the other demonstrates a progressive disease tumor growth pattern.

FIG. 8 compares for indication B, the response to both treatment schedules, the one originally suggested by the pharmaceutical company and the one recommended by Optimata. Optimata's recommended schedule demonstrates a better response, i.e. stable disease rather than progressive disease for the pharmaceutical company suggested schedule.

Figure 9:
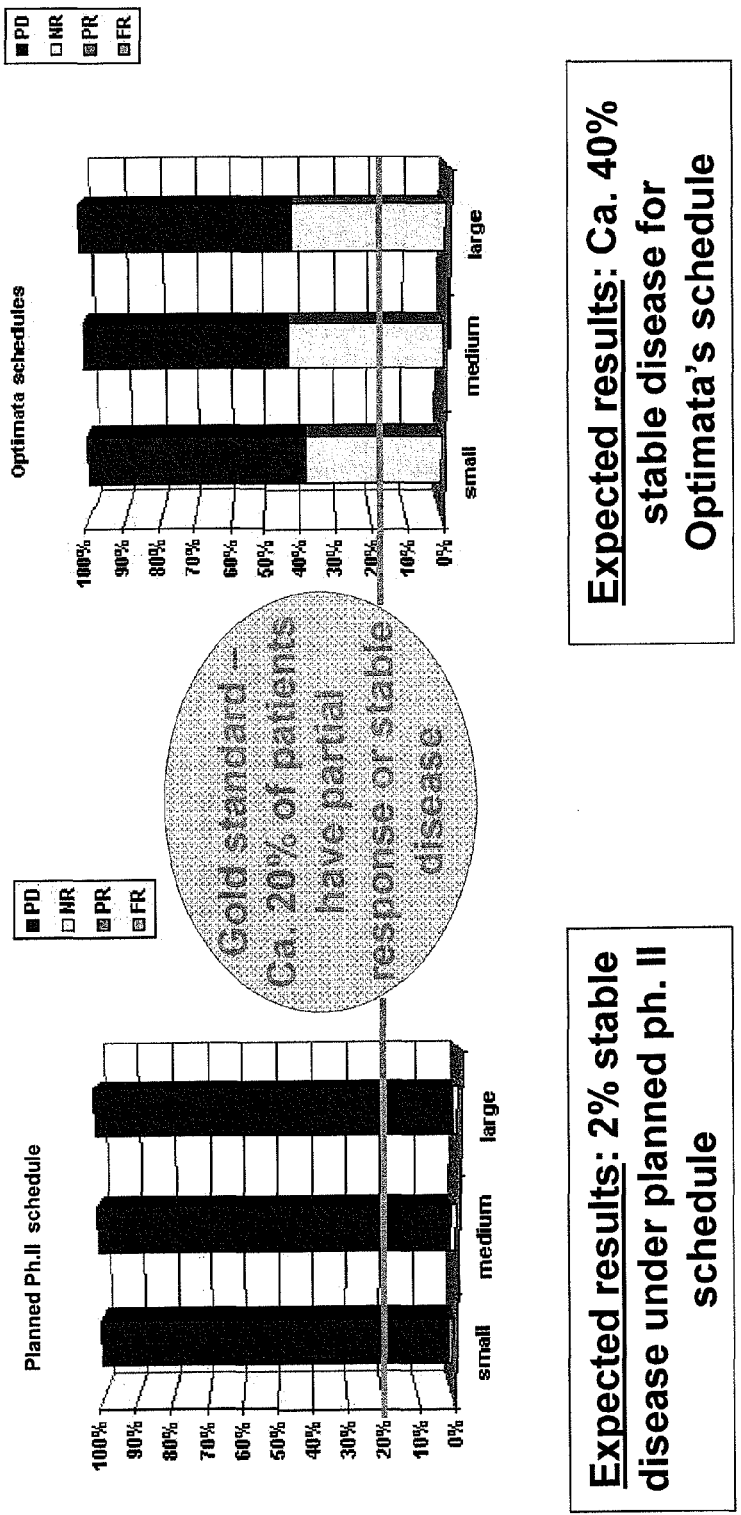
FIG. 9 shows predicted response to the gold standard schedule and the schedule recommended for indication B.

FIG. 9 provides a comparison of the response to the gold standard schedule for patients with indication B, with the response to the schedule recommended by Optimata for this indication. Optimata's recommended schedule demonstrates a better response, i.e. 40% stable disease while gold standard is predicted to have only 18% of overall response.

Figure 10:
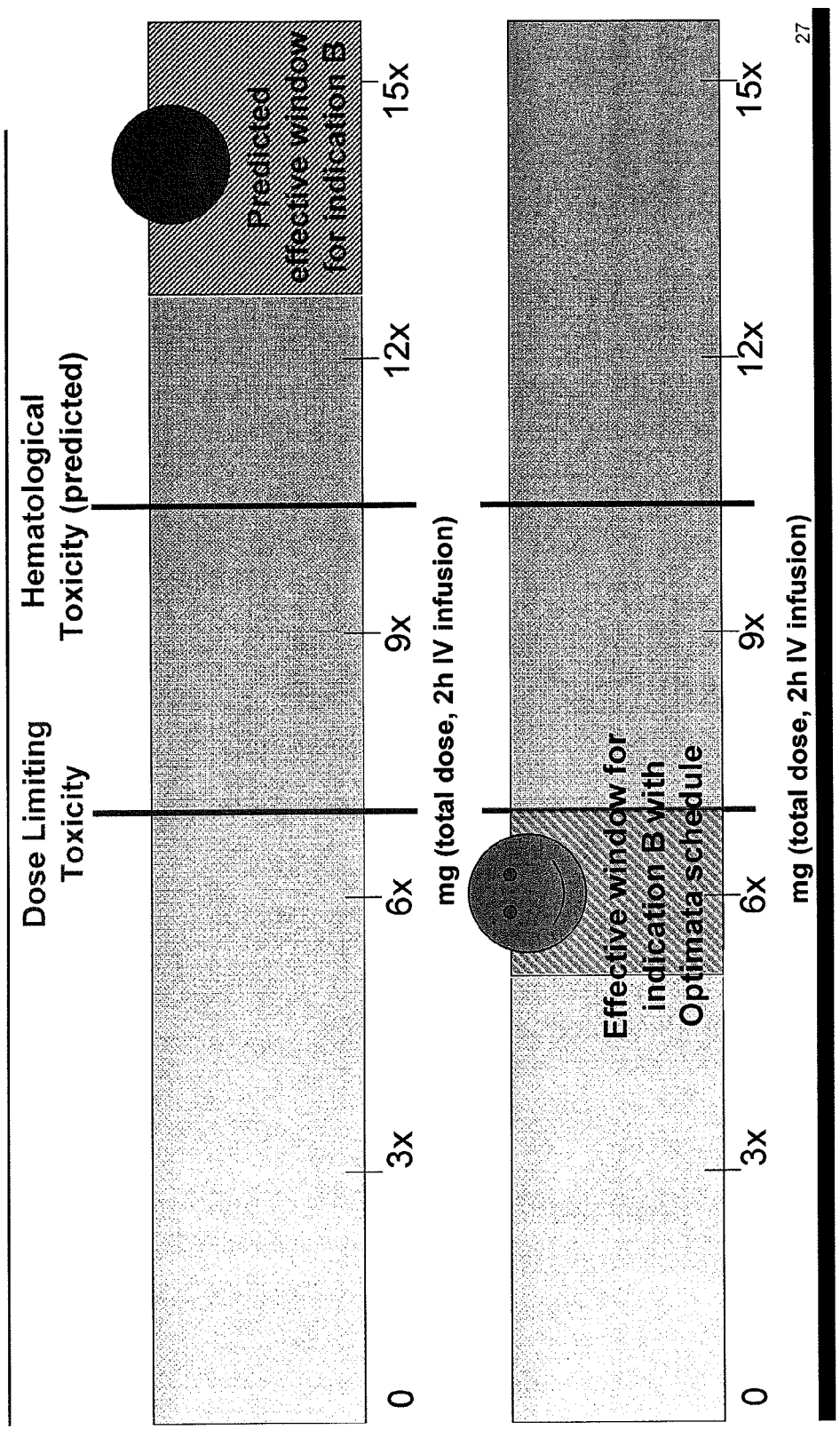
FIG. 10 shows the predicted effective therapeutic window for indication B with phase I schedule and with Optimata's recommended schedule.

FIG. 10 demonstrates that Optimata's suggested drug schedule agrees with the observed dose limiting toxicity, i.e., a clinically effective dose range.

Example B

Repurposing Marketed Drugs

The example below involves the repurposing of approved marketed drugs for the treatment of mesenchymal chondrosarcoma (MCS). As this clinical indication is a very rare type of cancer with few new cases per year a standard treatment doesn't exist. For this indication three targeted drugs were considered (Bevacizumab, Sunitinib, Sorafenib), as well as four chemotherapeutic drugs (Docetaxel, Gemcitabine, Doxorubicin and Irinotecan) see FIG. 11. Mono-therapies and various combination therapies of these 7 drugs were compared.

Predictions indicate several therapies, namely, a Bevacizumab+Docetaxel combination, to be significantly superior to others. Over the simulated treatment period of up to 41 days, combinations with Bevacizumab were predicted to greatly enhance the treatment efficacy in comparison to the corresponding monotherapies (see FIG. 13). Prediction results were compared to the corresponding experimental growth curves of treated and untreated tumor xenografts, derived from a lung metastasis of a MCS patient, for evaluating prediction accuracy. The average accuracy of the predictions was 82%. Furthermore, Sorafenib combined with Bevacizumab+Docetaxel greatly improved efficacy over a period of 120 days (see FIG. 15). These results were published in [Reference 3].

Thus, Bevacizumab, Docetaxel and Sorafenib were suggested to be repurposed for use as a combination therapy for MSC. Based on the simulations the best treatment schedule for this combination is also suggested. (see FIG. B6 below)

Docetaxel is approved to be used with other drugs to treat certain types of breast cancer, gastric cancer, and prostate cancer. Docetaxel is also approved to be used with other drugs to treat advanced squamous cell carcinoma of the head and neck (SCCHN) that cannot be removed by surgery.

Sorafenib is approved to treat advanced renal cell cancer (kidney cancer) in adults.

Bevacizumab is approved to be used with other drugs to treat colorectal cancer that has spread to other parts of the body. Bevacizumab is also approved to be used with other drugs to treat non-small cell lung cancer that cannot be removed by surgery, has spread to other parts of the body, or has recurred.

The above is demonstrated in the figures below as follows:

FIG. 11 lists the drugs for which mono and combination therapy was simulated.

FIG. 12 compares prediction results to corresponding experimental results of treated and untreated tumor xenografts, derived from a lung metastasis of a MCS patient. The average accuracy of the predictions was 82%.

Figure 13:
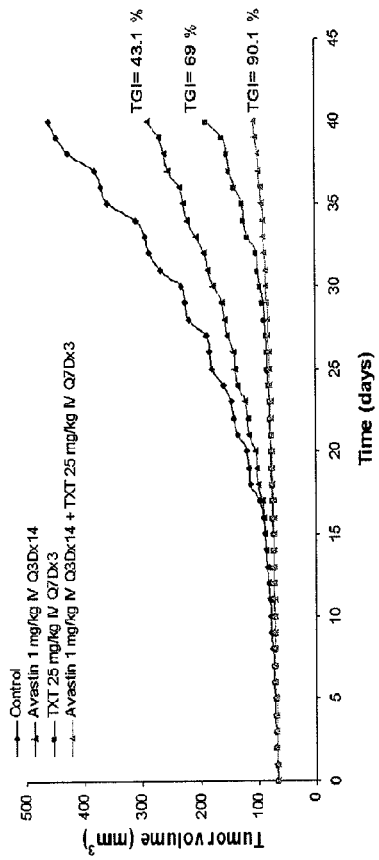
FIG. 13 shows prediction results of treatment efficacy with/without Bevacizumab (Avastin) over treatment period of up to 41 days.

FIG. 13 demonstrates that combination therapies with Bevacizumab were predicted to enhance the treatment efficacy in comparison to the corresponding monotherapies over treatment period of up to 41 days.

FIG. 14 demonstrates that Docetaxel Q1W+Bevacizumab Q2W was the most efficacious (slowest tumor growth) of all tested schedules over 120 day treatment.

Figure 15:
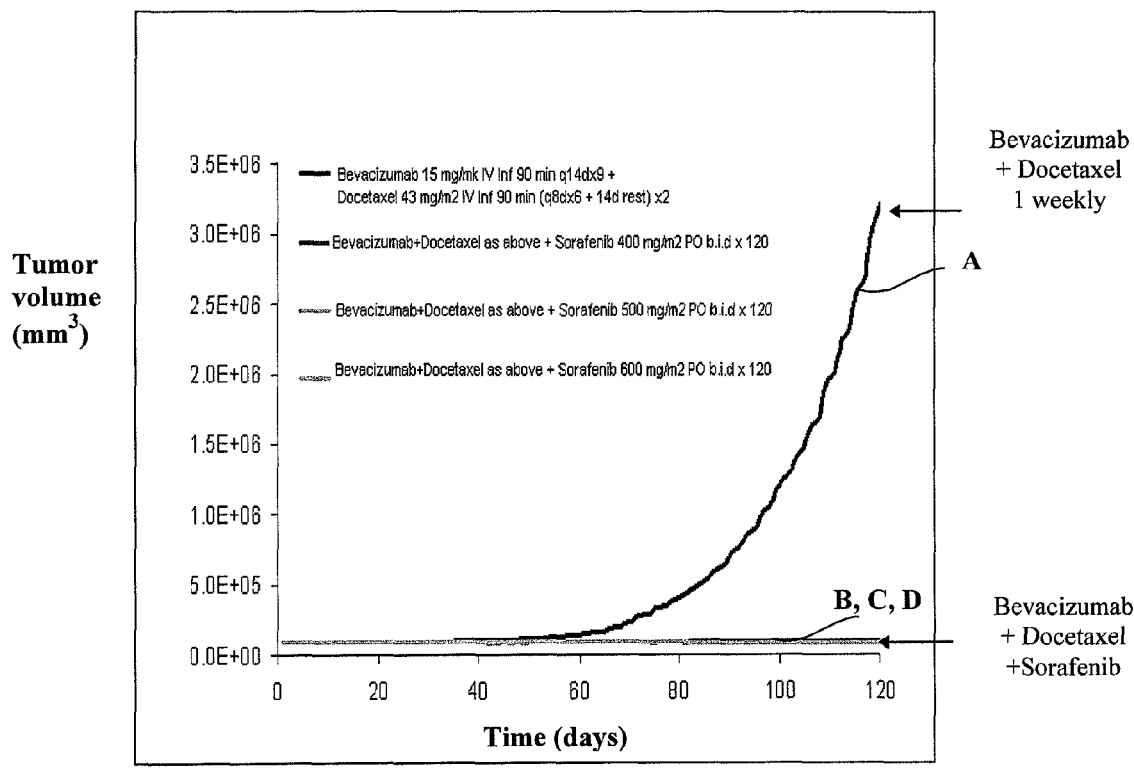
FIG. 15 shows that Surafenib combined with Bevacizumab+Docetaxel greatly improves efficacy over the period of 120 days.

FIG. 15 demonstrates that Surafenib combined with Bevacizumab+Docetaxel greatly improves efficacy over the period of 120 days.

Example C

Repurposing Marketed Drug in Combination with a Compound Under Development

In the example below, the above teachings are demonstrated to the repurpose an approved anti-angiogenic drug for use in combination with a cytotoxic drug under development.

Optimata's claimed method was used to determine a different indication A than the one currently used.

Figure 16:
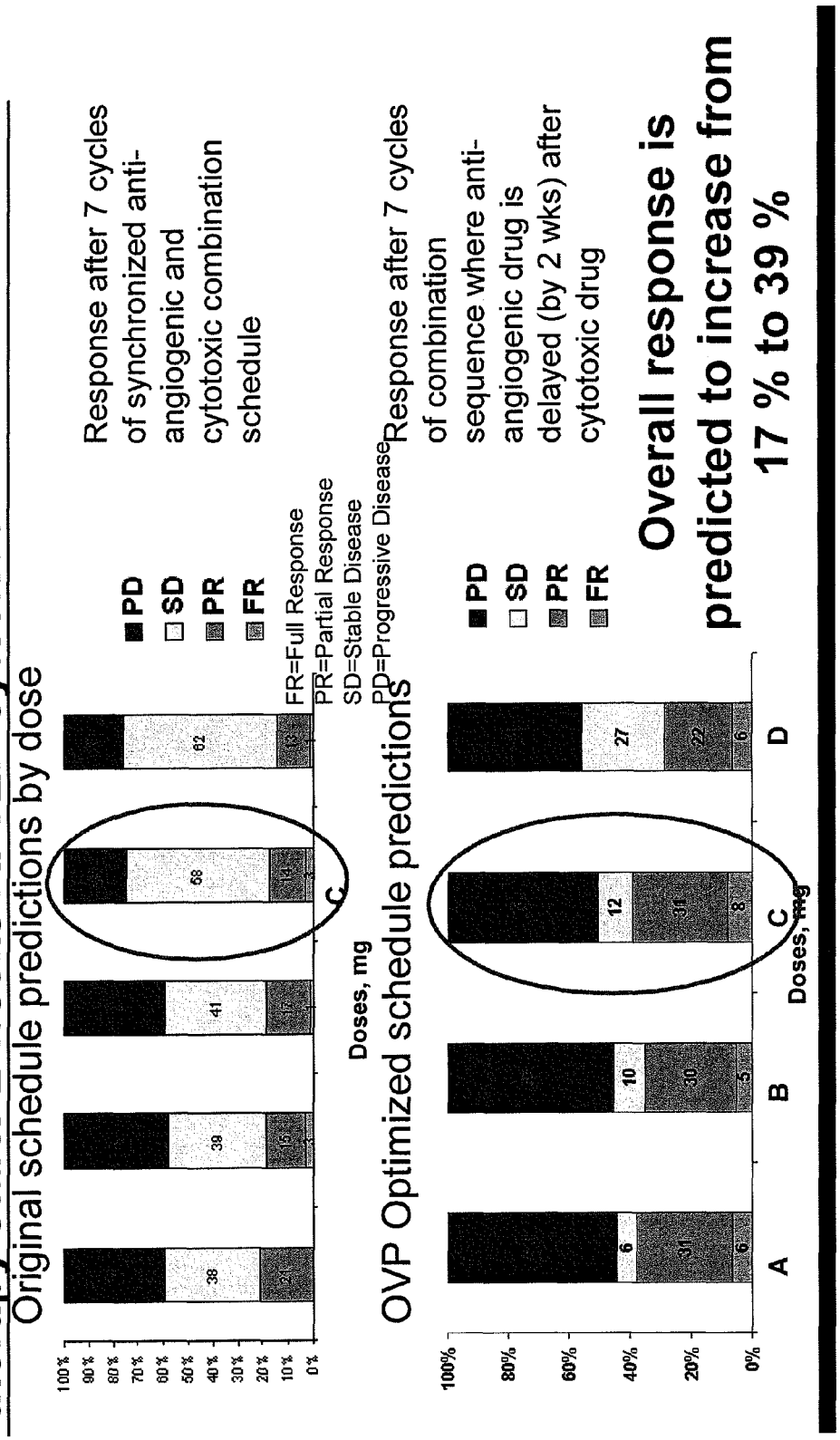
FIG. 16 shows predicted response of anti-angiogenic+cytotoxic synchronized therapy versus cytotoxic proceeded by anti-angiogenic therapy.
Figure 17:
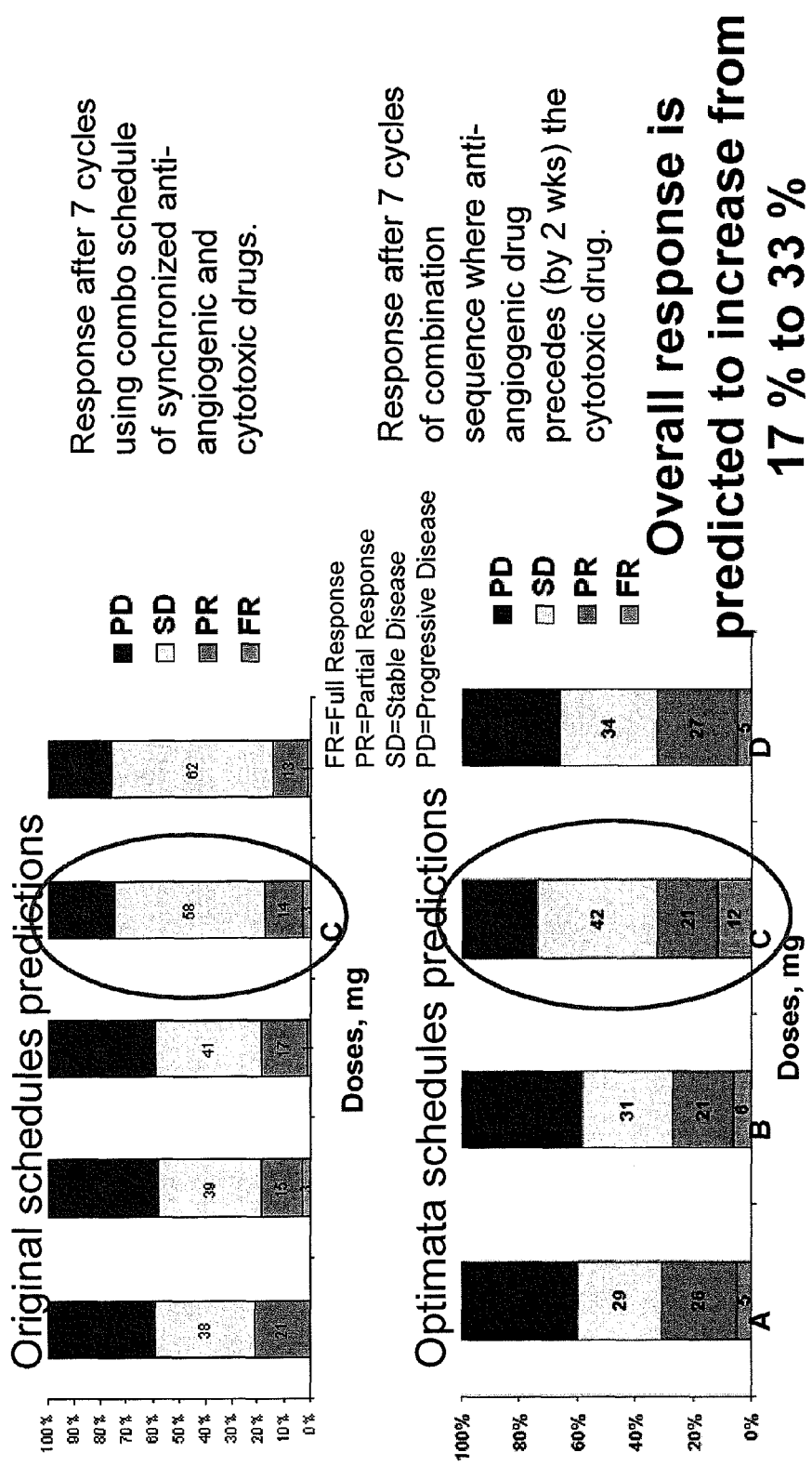
FIG. 17 shows predicted response of anti-angiogenic+cytotoxic synchronized therapy versus cytotoxic proceeded by anti-angiogenic therapy.

The claimed method was applied for indication A and the recommended new optimal schedule was predicted to be better than the response to gold standard treatment. Furthermore, the claimed method indicated that non-synchronized combination therapy (where the two drugs are not administered at the same time) increased the overall response (full+partial response) in comparison to the synchronized combination therapy (where the two drugs are administered together) suggested by the developer of the new drug (see FIGS. 16 and 17 below). The non-synchronized combination therapy also showed better recovery from the toxic effects (drop in neutrophils counts) with the same efficacy.

Other modifications and variations to the invention will be apparent to those skilled in the art from the foregoing disclosure and teachings. Thus, while only certain embodiments of the invention have been specifically described herein, it will be apparent that numerous modifications may be made thereto without departing from the spirit and scope of the invention.

What is claimed is:

1. A method for repurposing a pharmaceutical compound, resulting in a new treatment protocol to salvage a failed drug or an approved drug, the method comprising:
   a) identifying a pharmaceutical compound, wherein the pharmaceutical compound is a drug that has failed in clinical development or an approved drug;
   b) creating a computer model for pharmacokinetics and pharmacodynamics of the drug from in vitro or in vivo data obtained from administration of at least a single dose of the drug of (a) from a pre-clinical trial wherein the computer model created is adjusted based on data from in vitro or in vivo studies in animals;
   c) performing computer simulations using the computer model with data obtained from administration of different doses of the drug and dosing intervals for different indications and patient populations in at least one phase I clinical trial;
   wherein the computer model is an in silico patient that is adjusted according to results of the pre-clinical trial or the at least one phase I clinical trial.

2. The method of claim 1, wherein the new treatment protocol is based on at least one component selected from the group consisting of new regimen, new drug combination, new disease, new patient population, and use of biomarkers represented in the computer model to differentiate between responders and non-responders in the patient population.

3. The method of claim 2, wherein the new disease is cancer.

4. The method of claim 2, wherein the new disease is a hematological disorder.

5. The method of claim 2, wherein the new disease is a hematological disorder that is related to cancer.

6. The method of claim 1, wherein the new treatment protocol reduces drug toxicity.

7. The method of claim 1, wherein the new treatment protocol increases drug efficacy.

8. The method of claim 1, wherein the new treatment protocol increases drug efficacy and reduces drug toxicity.

9. The method of claim 1, wherein in step (c), the computer simulations of the model are performed prior to the phase I clinical trial, to obtain predicted phase I clinical trial results which are compared to the phase I clinical trial results and the computer model is adjusted based on the comparison.

10. The method of claim 1, wherein the different doses of the drug of step (c) are incrementally increased in at least one dose escalation step.

11. The method of claim 10, wherein the dose escalation step is calculated by computer simulations performed using the computer model in step (b) to obtain a maximal tolerated dose, minimum effective dose, and a recommended dose.

12. The method of claim 1, wherein the computer model is adjusted based on whether the clinical trial indicates a result higher than a threshold in at least one of pre-clinical trial and phase I clinical trial.

13. A method for repurposing a pharmaceutical compound, resulting in a new treatment protocol to salvage a failed drug or an approved drug, the method comprising
   creating a computer model for pharmacokinetics and pharmacodynamics of a drug that has failed in clinical development or an approved drug from in vitro or in vivo data obtained from administration of at least a single dose of the drug from at least one clinical trial to predict one or more clinical outcomes;
   wherein the prediction of one or more clinical outcomes is compared with clinical results from at least one clinical trial and the comparison is used to adjust the computer model,
   wherein the computer model is an in silico patient that is adjusted according to the clinical results at least from at least one pre-clinical trial; and
   wherein a new treatment protocol to salvage the failed drug or the approved drug is determined based on computer simulation results.

14. The method of claim 13, wherein the clinical results from at least one clinical trial is further selected from the group consisting of pre-clinical trial, phase I clinical trial, phase II clinical trial, phase III clinical trial, and phase IV clinical trial.

15. A method for repurposing a pharmaceutical compound, resulting in a new treatment protocol to salvage a failed drug or an approved drug, the method comprising
   creating a computer model for pharmacokinetics and pharmacodynamics of a drug that has failed in clinical development or an approved drug from in vitro or in vivo data obtained from administration of at least a single dose of the drug from at least one clinical trial to predict one or more clinical outcomes;
   wherein the prediction of one or more clinical outcomes is compared with clinical results from at least one clinical trial and the comparison is used to adjust the computer model, wherein the computer model is an in silico patient that is adjusted according to the clinical results at least from at least one phase I clinical trial; and
   wherein a new treatment protocol to salvage the failed drug or the approved drug is determined based on results of the computer simulation predictions.

16. The method of claim 15, wherein the at least a single dose is administered in a dose-escalation during phase I clinical trial.

17. The method of claim 15, wherein the clinical results from at least one clinical trial is further selected from the group consisting of pre-clinical trial, phase I clinical trial, phase II clinical trial, phase III clinical trial, and phase IV clinical trial.

18. A method for repurposing a pharmaceutical compound, resulting in a new treatment protocol to salvage a failed drug or an approved drug, the method comprising
   creating a computer model for pharmacokinetics and pharmacodynamics of a drug that has failed in clinical development or an approved drug from in vitro or in vivo data obtained from administration of at least a single dose of the drug from at least one clinical trial to predict one or more clinical outcomes;
   wherein the prediction of one or more clinical outcomes is compared with clinical results from at least one clinical trial and the comparison is used to adjust the computer model, wherein the computer model is an in silico patient that is adjusted according to the clinical results at least from at least phase II clinical trial; and
   wherein a new treatment protocol to salvage the failed drug or the approved drug is determined based on the computer simulation results.

19. The method of claim 18, wherein the clinical results from at least one clinical trial is further selected from the group consisting of pre-clinical trial, phase I clinical trial, phase II clinical trial, phase III clinical trial, and phase IV clinical trial.

20. A method for repurposing a pharmaceutical compound, resulting in a new treatment protocol to salvage a failed drug or an approved drug, the method comprising
creating a computer model for pharmacokinetics and pharmacodynamics of a drug that has failed in clinical development or an approved drug from in vitro or in vivo data obtained from administration of at least a single dose of the drug from at least one clinical trial to predict one or more clinical outcomes;
wherein the prediction of one or more clinical outcomes is compared with clinical results from at least one clinical trial and the comparison is used to adjust the computer model, wherein the computer model is an in silico patient that is adjusted according to the clinical results at least from at least one phase III clinical trial; and
wherein a new treatment protocol to salvage the failed drug or the approved drug is determined based on the computer simulation results.

21. The method of claim 20, wherein the clinical results from at least one clinical trial is further selected from the group consisting of pre-clinical trial, phase I clinical trial, phase II clinical trial, phase III clinical trial, and phase IV clinical trial.

22. A method for repurposing a pharmaceutical compound, resulting in a new treatment protocol to salvage a failed drug or an approved drug, the method comprising
creating a computer model for pharmacokinetics and pharmacodynamics of a drug that has failed in clinical development or an approved drug from in vitro or in vivo data obtained from administration of at least a single dose of the drug from at least one clinical trial to predict post-marketing efficacy of the drug, and long term efficacy of the drug, resulting in prediction of one or more clinical outcomes;
wherein the prediction of one or more clinical outcomes is compared with clinical results from at least one clinical trial and the comparison is used to adjust the computer model, wherein the computer model is an in silico patient that is adjusted according to the clinical results at least from at least one phase IV clinical trial; and
wherein a new treatment protocol to salvage the failed drug or the approved drug is determined based on the computer simulation results.

23. The method of claim 22, wherein the clinical results from at least one clinical trial is further selected from the group consisting of pre-clinical trial, phase I clinical trial, phase II clinical trial, phase III clinical trial, and phase IV clinical trial.

24. A system for repurposing a pharmaceutical compound, the system comprising:
identifying a pharmaceutical compound, wherein the pharmaceutical compound is a drug that has failed in clinical development or an approved drug;
a computer model for pharmacokinetics and pharmacodynamics of the drug is created based on data of effects of the drug administered in vitro or in vivo to determine the physiological effect of the drug on a disease;
a model adjustor that adjusts the computer model based upon results of computer simulations from at least one pre-clinical or at least one clinical trial;
a treatment protocol generator that determines a new treatment protocol to salvage the drug that has failed in a clinical development or the approved drug.

25. The system of claim 24, wherein the new treatment protocol is based on at least one component selected from the group consisting of new regimen, new drug combination, new disease, new patient population, and use of biomarkers represented in the computer model to differentiate between responders and non-responders in the patient population.

26. The system of claim 24, wherein the new treatment protocol is a drug combination.

27. The system of claim 24, wherein the new disease is cancer.

28. The system of claim 24, wherein the new disease is a hematological disorder.

29. The system of claim 24, wherein the new disease is a hematological disorder that is related to cancer.

30. The system of claim 24, wherein the new treatment protocol reduces drug toxicity.

31. The system of claim 24, wherein the new treatment protocol increases drug efficacy.

32. The system of claim 24, wherein the new treatment protocol increases drug efficacy and reduces drug toxicity.

33. A computer program product comprising a non-transitory computer readable media having instructions that allows a computer to implement a process comprising:
a) identifying a pharmaceutical compound, the pharmaceutical compound corresponding to a drug that has failed in clinical development or an approved drug;
b) creating a computer model for pharmacokinetics and pharmacodynamics of the drug based on data of effects of the drug administered in vitro or in vivo to determine the physiological effect of the drug on a disease;
c) adjusting the computer model based upon results of computer simulations from at least one pre-clinical or at least one clinical trial;
d) determining a new treatment protocol to salvage the failed drug or the approved drug based on the results of computer simulation results; and
e) displaying the new treatment protocol in an output window.

* * * * *